United States Patent
Ko et al.

(10) Patent No.: US 12,188,082 B2
(45) Date of Patent: Jan. 7, 2025

(54) METHOD AND APPARATUS FOR DETECTING A PLURALITY OF TARGET NUCLEIC ACID SEQUENCES IN SAMPLE

(71) Applicant: SEEGENE, INC., Seoul (KR)

(72) Inventors: Sung Moon Ko, Seoul (KR); Ji Hye Han, Seoul (KR); Young Wook Kim, Seoul (KR); Young Yong Park, Seoul (KR)

(73) Assignee: SEEGENE, INC., Seoul (KR)

( * ) Notice: Subject to any disclaimer, the term of this patent is extended or adjusted under 35 U.S.C. 154(b) by 1136 days.

(21) Appl. No.: 17/043,198

(22) PCT Filed: Apr. 19, 2019

(86) PCT No.: PCT/KR2019/004780
§ 371 (c)(1),
(2) Date: Sep. 29, 2020

(87) PCT Pub. No.: WO2019/203623
PCT Pub. Date: Oct. 24, 2019

(65) Prior Publication Data
US 2021/0040542 A1 Feb. 11, 2021

(30) Foreign Application Priority Data
Apr. 20, 2018 (KR) .................. 10-2018-0046375

(51) Int. Cl.
*C12Q 1/6816* (2018.01)
*G16B 40/10* (2019.01)

(52) U.S. Cl.
CPC .......... *C12Q 1/6816* (2013.01); *G16B 40/10* (2019.02); *C12Q 2527/107* (2013.01); *C12Q 2537/143* (2013.01)

(58) Field of Classification Search
CPC .. C12Q 1/68; C12Q 1/6816; C12Q 2527/107; C07H 21/00; G16B 40/10
See application file for complete search history.

(56) References Cited

U.S. PATENT DOCUMENTS

| | | | |
|---|---|---|---|
| 5,210,015 A | 5/1993 | Gelfand et al. | |
| 5,538,848 A | 7/1996 | Livak et al. | |
| 6,117,635 A | 9/2000 | Nazarenko et al. | |
| 6,977,295 B2 | 12/2005 | Belotserkovskii et al. | |
| 8,039,215 B2 | 10/2011 | Higuchi et al. | |
| 9,493,835 B2 | 11/2016 | Reis, Jr. et al. | |
| 2004/0121371 A1 | 6/2004 | Andersen et al. | |
| 2005/0053950 A1 | 3/2005 | Zudaire Ubani et al. | |
| 2006/0177841 A1 | 8/2006 | Wangh et al. | |
| 2013/0109588 A1* | 5/2013 | Chun ................. | C12Q 1/6853 506/9 |
| 2017/0362646 A1 | 12/2017 | Chun et al. | |
| 2018/0073056 A1 | 3/2018 | Kozlov et al. | |
| 2018/0336315 A1* | 11/2018 | Chun ................. | G16B 50/00 |

FOREIGN PATENT DOCUMENTS

| | | |
|---|---|---|
| WO | WO-2012/096523 A2 | 7/2012 |
| WO | WO-2013/115442 A1 | 8/2013 |
| WO | WO-2014/104818 A1 | 7/2014 |
| WO | WO-2015/147370 A1 | 10/2015 |
| WO | WO-2015/147412 A1 | 10/2015 |
| WO | WO-2017/188669 A2 | 11/2017 |
| WO | WO-2019/066461 A2 | 4/2019 |

OTHER PUBLICATIONS

Wittwer et al, Real-time Multiplex Assays. Methods 25:430 (Year: 2001).*
Bernard, P.S., et al. (1999) "Color Multiplexing Hybridization Probes Using the Apolipoprotein E Locus as a Model System for Genotyping.", *Anal. Biochem.*, 273:221-228.
French, D.J., et al. (2001) "HyBeaconTM probes: a new tool for DNA sequence detection and allele discrimination.", *Mol. Cell Probes*, 15(6):363-374.
Li, et al. (2002) "A new class of homogeneous nucleic acid probes based on specific displacement hybridization.", *Nucleic Acids Research*, 30(2)(e5):1-9.
Nazarenko, et al. (1997) "A closed tube format for amplification and detection of DNA based on energy transfer.", *Nucleic Acids Research*, 25(12):2516-2521.
Sherrill, C. B., et al. (2004) "Nucleic Acid Analysis Using an Expanded Genetic Alphabet to Quench Fluorescence.", *Journal of the American Chemical Society*, 126:4550-4556.
Tyagi, et al. (1996) "Molecular Beacons: Probes that Fluoresce upon Hybridization.", *Nature Biotechnology*, 14(3):303-308.
Whitcombe, et al. (1999) "Detection of PCR products using selfprobing amplicons and fluorescence.", *Nature Biotechnology*, 17:804-807.
International Search Report from corresponding PCT Application No. PCT/KR2019/004780, dated Aug. 19, 2019.

* cited by examiner

*Primary Examiner* — Ethan C Whisenant
(74) *Attorney, Agent, or Firm* — Harness, Dickey & Pierce, P.L.C.

(57) ABSTRACT

The method of the present invention enables efficient detection of a plurality of target nucleic acid sequences in one detection channel, by obtaining a data set of cycle/signal-change value.

34 Claims, 12 Drawing Sheets
Specification includes a Sequence Listing.

$$RFU(T,C) = f(T)\, g(C) + \alpha$$

<CT 10^6>

<CT 10^4>

<CT 10^3>

<CT 10^2>

<CT 10^4>

<TP 10^4>

<CT 10^4 >          <TP 10^3 >

<CT 10^4>        <TP 10^2>

<CT 10^2>

<TP 10^4>

SEQUENCE LISTING

<160> NUMBER OF SEQ ID NOS: 12

<210> SEQ ID NO 1
<211> LENGTH: 35
<212> TYPE: DNA
<213> ORGANISM: Artificial Sequence
<220> FEATURE:
<223> OTHER INFORMATION: Synthetic nucleotide: 33-F
<220> FEATURE:
<221> NAME/KEY: misc_feature
<222> LOCATION: (22)..(26)
<223> OTHER INFORMATION: n is deoxyinosine

<400> SEQUENCE: 1
aatggtattt gttggggcaa tnnnnnattt gttac                          35

<210> SEQ ID NO 2
<211> LENGTH: 37
<212> TYPE: DNA
<213> ORGANISM: Artificial Sequence
<220> FEATURE:
<223> OTHER INFORMATION: Synthetic nucleotide: 33-R
<220> FEATURE:
<221> NAME/KEY: misc_feature
<222> LOCATION: (6)..(6)
<223> OTHER INFORMATION: n is deoxyinosine
<220> FEATURE:
<221> NAME/KEY: misc_feature
<222> LOCATION: (13)..(13)
<223> OTHER INFORMATION: s is guanine or cytosine
<220> FEATURE:
<221> NAME/KEY: misc_feature
<222> LOCATION: (24)..(28)
<223> OTHER INFORMATION: n is deoxyinosine

<400> SEQUENCE: 2
tcctgnaaac tascagatgg aggnnnnntt aaaccaa                        37

<210> SEQ ID NO 3
<211> LENGTH: 49
<212> TYPE: DNA
<213> ORGANISM: Artificial Sequence
<220> FEATURE:
<223> OTHER INFORMATION: Synthetic nucleotide: 33-PTO
<220> FEATURE:
<221> NAME/KEY: misc_feature
<222> LOCATION: (20)..(20)
<223> OTHER INFORMATION: r is adenine or guanine

<400> SEQUENCE: 3
aacggtacga cggcacacar gtaactagtg acagtacata taaaaatga           49

<210> SEQ ID NO 4
<211> LENGTH: 38
<212> TYPE: DNA
<213> ORGANISM: Artificial Sequence
<220> FEATURE:
<223> OTHER INFORMATION: Synthetic nucleotide: 33-CTO

<400> SEQUENCE: 4
ttatatttta tttattata tactgccgtc gtaccgtt                        38

<210> SEQ ID NO 5
<211> LENGTH: 40
<212> TYPE: DNA
<213> ORGANISM: Artificial Sequence
<220> FEATURE:
<223> OTHER INFORMATION: Synthetic nucleotide: 39-F
<220> FEATURE:
<221> NAME/KEY: misc_feature

```
<222> LOCATION: (3)..(3)
<223> OTHER INFORMATION: y is cytosine or thymine
<220> FEATURE:
<221> NAME/KEY: misc_feature
<222> LOCATION: (27)..(31)
<223> OTHER INFORMATION: n is deoxyinosine

<400> SEQUENCE: 5
gayactaccc gtagtaccaa ctttacnnnn nctacctcta                              40

<210> SEQ ID NO 6
<211> LENGTH: 33
<212> TYPE: DNA
<213> ORGANISM: Artificial Sequence
<220> FEATURE:
<223> OTHER INFORMATION: Synthetic nucleotide: 39-R
<220> FEATURE:
<221> NAME/KEY: misc_feature
<222> LOCATION: (20)..(24)
<223> OTHER INFORMATION: n is deoxyinosine
<220> FEATURE:
<221> NAME/KEY: misc_feature
<222> LOCATION: (27)..(27)
<223> OTHER INFORMATION: r is adenine or guanine

<400> SEQUENCE: 6
ctggcagatg gtggaggagn nnnngcraaa ttc                                    33

<210> SEQ ID NO 7
<211> LENGTH: 42
<212> TYPE: DNA
<213> ORGANISM: Artificial Sequence
<220> FEATURE:
<223> OTHER INFORMATION: Synthetic nucleotide: 39-PTO
<220> FEATURE:
<221> NAME/KEY: misc_feature
<222> LOCATION: (28)..(28)
<223> OTHER INFORMATION: k is guanine or thymine
<220> FEATURE:
<221> NAME/KEY: misc_feature
<222> LOCATION: (29)..(29)
<223> OTHER INFORMATION: r is adenine or guanine

<400> SEQUENCE: 7
acggcgcaat acctcctcca cgtgcctkrt atattcctta aa                          42

<210> SEQ ID NO 8
<211> LENGTH: 38
<212> TYPE: DNA
<213> ORGANISM: Artificial Sequence
<220> FEATURE:
<223> OTHER INFORMATION: Synthetic nucleotide: 39-CTO

<400> SEQUENCE: 8
tattattatt aagagctgct tccgaggtat tgcgccgt                               38

<210> SEQ ID NO 9
<211> LENGTH: 33
<212> TYPE: DNA
<213> ORGANISM: Artificial Sequence
<220> FEATURE:
<223> OTHER INFORMATION: Synthetic nucleotide: 52-F
<220> FEATURE:
<221> NAME/KEY: misc_feature
<222> LOCATION: (20)..(24)
<223> OTHER INFORMATION: n is deoxyinosine

<400> SEQUENCE: 9
cagggccaca ataatggcan nnnntggggc aat                                    33
```

```
<210> SEQ ID NO 10
<211> LENGTH: 34
<212> TYPE: DNA
<213> ORGANISM: Artificial Sequence
<220> FEATURE:
<223> OTHER INFORMATION: Synthetic nucleotide: 52-R
<220> FEATURE:
<221> NAME/KEY: misc_feature
<222> LOCATION: (22)..(26)
<223> OTHER INFORMATION: n is deoxyinosine
<220> FEATURE:
<221> NAME/KEY: misc_feature
<222> LOCATION: (32)..(32)
<223> OTHER INFORMATION: w is adenine or thymine

<400> SEQUENCE: 10
cctttccttt aggtggtgtg tnnnnntgac awgt                              34

<210> SEQ ID NO 11
<211> LENGTH: 44
<212> TYPE: DNA
<213> ORGANISM: Artificial Sequence
<220> FEATURE:
<223> OTHER INFORMATION: Synthetic nucleotide: 52-PTO
<220> FEATURE:
<221> NAME/KEY: misc_feature
<222> LOCATION: (40)..(40)
<223> OTHER INFORMATION: y is cytosine or thymine

<400> SEQUENCE: 11
tgtcgatcgc gtccagtcct ctaaaatagt ggcatccaty ttat                   44

<210> SEQ ID NO 12
<211> LENGTH: 38
<212> TYPE: DNA
<213> ORGANISM: Artificial Sequence
<220> FEATURE:
<223> OTHER INFORMATION: Synthetic nucleotide: 52-CTO

<400> SEQUENCE: 12
tgcgatatgt cgggtacgac tggtggacgc gatcgaca                          38
```

METHOD AND APPARATUS FOR DETECTING A PLURALITY OF TARGET NUCLEIC ACID SEQUENCES IN SAMPLE

CROSS-REFERENCE TO RELATED APPLICATIONS

This application is a national phase application of PCT Application No. PCT/KR2019/004780, filed on Apr. 19, 2019, which claims priority to Korean Patent Application No. 10-2018-0046375, filed on Apr. 20, 2018. The entire disclosures of the applications identified in this paragraph are incorporated herein by references.

BACKGROUND OF THE INVENTION

Field of the Invention

The present invention relates to detection of a plurality of target nucleic acid sequences using a signal-change value.

Description of the Related Art

A real-time PCR is one of PCR-based technologies for detecting a target nucleic acid molecule in a sample in a real-time manner (Logan 3 et al., (2009). Real Time PCR: Current Technology and Applications. Caister Academic Press). For detecting a target nucleic acid molecule, the real-time PCR uses signal-generating compositions for generating a fluorescent signal being detectable in a proportional manner with the amount of the target molecule. The generation of fluorescent signals may be accomplished by using either intercalators generating signals when intercalated between double-stranded DNA or oligonucleotides carrying fluorescent reporter and quencher molecules. The fluorescent signals whose intensities are proportional with the amount of the target molecule are detected at each amplification cycle and plotted against amplification cycles, thereby obtaining an amplification curve or amplification profile curve.

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. As alternative approaches, real-time detection methods using duplexes formed depending on the presence of target nucleic acid sequences have been proposed.

The conventional real-time detection technologies described above detect signals generated from fluorescent labels at a selected detection temperature in signal amplification process associated with or with no target amplification. When a plurality of target nucleic acid sequences using a single type of label in a single reaction tube are detected in accordance with the conventional real-time detection technologies, generated signals for target nucleic acid sequences are not differentiated from each other. Therefore, the conventional real-time detection technologies generally employ different types of labels for detecting a plurality of target nucleic acid sequences. The melting analysis using $T_m$ difference permits to detect a plurality of target nucleic acid sequences even a single type of label. However, the melting analysis has serious shortcomings in that its performance time is longer than real-time technologies and design of probes with different $T_m$ values becomes more difficult upon increasing target sequences. In addition, the melting analysis has a limitation in the quantification application as it does not provide Ct values unlike the real-time detection method.

Novel methods or approaches being not dependent on melting analysis for detecting a plurality of target nucleic acid sequences using labels having an identical signal property in a single reaction vessel and a single type of detector are developed.

W.O. Pub. No. 2015/147412 discloses a method for detecting a plurality of target nucleic acid sequences in a sample using different detection temperatures. The method is characterized in as measuring signals at detection temperatures of which number is the same as number of the target nucleic acid sequences to be detected. The method has an advantage using a small number of the detection temperatures per one target nucleic acid sequence but relatively distantly separate detection temperatures should be selected to meet the detection temperature requirements.

U.S. Pub. NO 2005/0053950 discloses a method for detecting target nucleic acid sequences using amplicons thereof and an intercalating dye. The method adopts the difference of Tm values between the amplicons for detection. However, it is difficult to adjust the Tm values of the amplicons for the different target nucleic acid sequences. Furthermore, the amplicons have relatively long nucleotide length, which constrains them to induce sufficient signal changes in a narrow temperature change in detection temperatures.

U.S. Pat. No. 8,039,215 describes a method for performing a melting analysis at every cycle and plotting melting peaks of targets at every cycle to produce amplification curves for the targets. The melting analysis at every cycle makes the process spend too much time.

Throughout this application, various patents and publications are referenced and citations are provided in parentheses. The disclosure of these patents and publications in their entireties are hereby incorporated by references into this application in order to more fully describe this invention and the state of the art to which this invention pertains.

SUMMARY OF THE INVENTION

The present inventors have made intensive researches to develop novel methods for detecting a plurality of target nucleic acid sequences using a label having an identical signal property in a single reaction vessel. As a result, we have found that a signal-change value calculated by signal values obtained from a duplex comprising a labeled oligonucleotide at two temperatures enables to determine the presence or absence of the plurality of target nucleic acid sequence.

Accordingly, it is an object of this invention to provide a method for detecting a plurality of target nucleic acid sequences using a signal-change value.

It is another object of this invention to provide a computer readable storage medium containing instructions to configure a processor to perform a method for determining the presence of a plurality of target nucleic acid sequences using a signal-change value.

It is still another object of this invention to provide a device for detecting a plurality of target nucleic acid sequences using a signal-change value.

It is a further object of this invention to provide a method for detecting a target nucleic acid sequences using a signal-change value.

It is still further object of this invention to provide a computer readable storage medium containing instructions to configure a processor to perform a method for determining the presence of a target nucleic acid sequence using a signal-change value.

It is still another object of this invention to provide a device for detecting a target nucleic acid sequences using a signal-change value.

Other objects and advantages of the present invention will become apparent from the detailed description to follow taken in conjugation with the appended claims and drawings.

DETAILED DESCRIPTION OF THIS INVENTION

Figure 1:
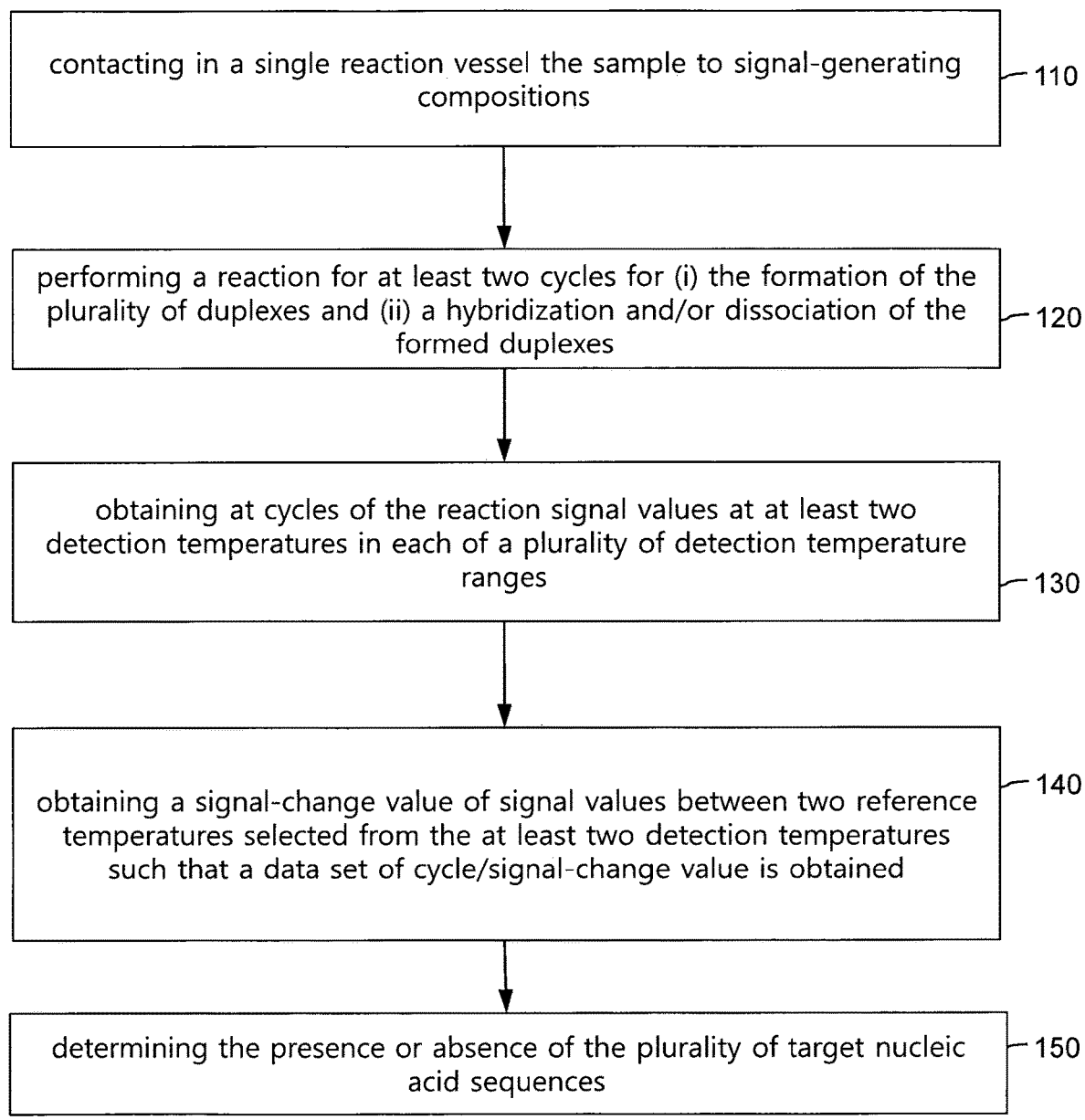
FIG. 1 is a flow chart illustrating an embodiment of a process for determining a presence or absence of the plurality of target nucleic acid sequences according to the present invention.

When a plurality of duplexes having different $T_m$ values, containing labels providing signals with the same signal property (e.g., the same wavelength band), are present in a single reaction vessel, the signal value detected at a particular detection temperature may include a combination of signals generated from the duplexes.

For each of duplexes for target nucleic acid sequences, there is a temperature range in which the intensity of the signal values varies with temperature, which depends on the $T_m$ value of each duplex. The signal values at temperatures within the temperature range in which the intensity of the signal from a target nucleic acid sequence varies with temperature and those from other target nucleic acid sequences do not may include signals from the other target nucleic acid sequences. The intensity of the signals contributed by the other target nucleic acid sequences are almost constant in the temperature range. The calculation of a signal-change value of signal values at two temperatures within the temperature range makes it possible to obtain only the signal-change value provided by the target nucleic acids sequence while the signal values provided by the other target nucleic acid sequences are eliminated during calculation. In other words, the signal-change value between two temperatures within the temperature range may be provided by a change of the amount of the duplex for the corresponding target nucleic acid sequence, which would indicate the presence of the corresponding target nucleic acid sequence.

The present inventors have found that the use of a duplex containing a labeled oligonucleotide, in particular a duplex formed in a dependent manner on a mediation oligonucleotide-involving cleavage enables the detection of a target nucleic acid sequence by a signal-change value between temperatures of relatively narrow intervals, e.g., at temperatures of about 2° C. to 5° C. (particularly, about 2° C. to 4° C.) intervals, together with sophisticated control of Tm values of the duplexes and with increasing duplex-dissociation or hybridization sensitivity to temperature changes. Further, it has also been found that the use of temperatures of narrow intervals allows a greater number of target nucleic acid sequences to be detected with a reduced risk of false positives. Moreover, the present inventors have adopted a method of selecting the reference temperatures to be used in the calculation of the signal-change value for each reaction in order to solve the problem that an expected $T_m$ value of the duplex may differ from a $T_m$ value in the actual reaction environment. Such approach can provide more accurate and reliable results, and more tolerant results to reaction-to-reaction variations.

I. Detection of a Plurality of Target Nucleic Acid Sequences in a Sample Using a Signal-Change Value in two Temperatures In one aspect of this invention, there is provided a method for detecting a plurality of target nucleic acid sequences in a sample, comprising:

contacting in a single reaction vessel the sample to signal-generating compositions for detecting the plurality of target nucleic acid sequences; wherein the signal-generating compositions form a plurality of duplexes for the plurality of target nucleic acid sequences, each of the plurality of duplexes provides a signal indicating the presence of each corresponding target nucleic acid sequence and the plurality of duplexes have $T_m$ values different from each other;

performing a reaction for at least two cycles for (i) the formation of the plurality of duplexes and (ii) a hybridization and/or dissociation of the formed duplexes;

obtaining at all or partial cycles of the reaction signal values at at least two detection temperatures in each of a plurality of detection temperature ranges assigned to the plurality of target nucleic acid sequences; wherein each of the plurality of detection temperature ranges comprises a temperature range in which the amount of a duplex for each corresponding target nucleic acid sequence is changed;

obtaining a signal-change value of signal values between two reference temperatures selected from the at least two detection temperatures in each of the plurality of detection temperature ranges such that a data set of cycle/signal-change value for each of the plurality of target nucleic acid sequences is obtained; and determining the presence or absence of the plurality of target nucleic acid sequences in the sample by the data set of cycle/signal-change value for each of the plurality of target nucleic acid sequences.

FIG. 1 is a flow chart for the present method. With reference to FIG. 1, the present invention will be described in more detail as follows:

Step: Contacting the Sample to Signal-Generating Compositions (110)

The sample to be analyzed is contacted to signal-generating compositions for detecting the plurality of target nucleic acid sequences in a single reaction vessel.

The term used herein "signal-generating composition" herein refers to a composition generating a signal indicating the presence of absence of the target nucleic acid sequence. Alternatively, The term used herein "signal-generating composition" herein refers to any materials used in generating a detectable signal in a dependent manner on the presence of the target nucleic acid sequence by a biological, biochemical or chemical reaction processes. Particularly, the term used herein "signal-generating composition" herein refers to any materials used in generating a detectable signal in a dependent manner on the formation of a duplex.

In an embodiment of the present invention, a signal-generating composition comprises materials used in formation of a duplex for the corresponding target nucleic acid sequence.

Each of the target nucleic acid sequences can be detected by a corresponding signal-generating composition. The first signal-generating composition may represent the materials used for detection of the first target nucleic acid sequence and the second signal-generating composition may represent the materials used for detection of the second target nucleic acid sequence and the like.

The duplex for the corresponding target nucleic acid sequence formed by the corresponding signal-generating composition provides a signal indicating the presence or absence of the corresponding target nucleic acid sequence.

The term used herein "a signal indicating the presence" can be used interchangeably with "a signal indicating the presence or absence" unless otherwise indicated.

The term used herein "signal generated by signal-generating composition" may refer to the signal from the duplex formed by the signal-generating composition.

A signal-generating composition for a target nucleic acid sequence may comprise one or more oligonucleotides. The one or more oligonucleotides may comprise one or more labeled oligonucleotides. A signal-generating composition for a target nucleic acid sequence may comprise one or more labeled oligonucleotides which are involved in formation of a duplex.

In an embodiment, one or more strands of a duplex are a labeled oligonucleotide. According to an embodiment, the duplex comprise at least one label on at least its one strand.

The term used herein "detection oligonucleotide" is an oligonucleotide which is involved in generation of signal to be detected. According to an embodiment, the detection oligonucleotide includes an oligonucleotide which is involved in an actual signal generation. According to an embodiment, the detection oligonucleotide comprises at least one label. According to an embodiment, the labeled oligonucleotide involved in forming a duplex and generating a signal is a detection oligonucleotide.

According to an embodiment of the present invention, the signal generating compositions of the present method generates a signal in a dependent manner on the formation of a duplex Various methods generating a signal in a dependent manner on the formation of a duplex are known and the signal-generating compositions of the present method may contain materials required to perform the methods.

The expression used herein "generate a signal in a dependent manner on the formation of a duplex" in conjunction with signal-generating compositions refers to that signal to be detected is provided being dependent on association or dissociation of two nucleic acid molecules. The expression includes that a signal is provided by a duplex (e.g. a detection oligonucleotide with a label and a nucleic acid sequence) formed being dependent on the presence of a target nucleic acid sequence. In addition, the expression includes that a signal is provided by inhibition of hybridization of a duplex (e.g. a detection oligonucleotide with a label and a nucleic acid sequence) wherein the inhibition is caused by the formation of another duplex.

The term used herein "the formation of a duplex" include the formation of a duplex by producing one or more strands comprised of the duplex during a reaction as well as the formation of a duplex by hybridizing two strands present before a reaction in a hybridization condition.

One of the most prominent features of the present invention is characterized in adopting a duplex including a labeled oligonucleotide, instead of using an amplicon, an amplification product of a target nucleic acid sequence.

The present invention uses Tm value of the duplex containing a labeled oligonucleotide not Tm value of the amplicon of the target nucleic acid sequence.

It is relatively difficult to adjust a Tm value of an amplicon to a desired Tm value. In addition, temperature ranges available for detecting a plurality of target nucleic acid sequences are limited as Tm values of amplicons are likely to be in relatively high temperature range. Furthermore, an intercalating dye used for labeling the amplicon of target nucleic acid sequences is incorporated into a non-specific product, which causes a false signal. According to an embodiment, the present invention does not use an intercalating dye.

Duplexes formed by the signal-generating compositions of the present method may be (i) a duplex formed by hybridization between the target nucleic acid sequence and a labeled oligonucleotide, (ii) a duplex formed by hybridization between an oligonucleotide comprising a hybridizing sequence complementary to the target nucleic acid sequence and a labeled oligonucleotide complementary to at least a portion of the hybridizing sequence or (iii) a duplex formed in a dependent manner on a mediation oligonucleotide-involving cleavage wherein the mediation oligonucleotide is the hybridized with the target nucleic acid sequence.

Particularly, a duplex is formed between a target nucleic acid sequence and a labeled oligonucleotide specifically hybridized with the target nucleic acid sequence.

The formation of a duplex between a target nucleic acid sequence and the labeled oligonucleotide may be generated by various methods, including Scorpion method (Whitcombe et al, Nature Biotechnology 17:804-807 (1999)), Sunrise (or Amplifluor) method (Nazarenko et al, Nucleic Acids Research, 25(12):2516-2521 (1997), and U.S. Pat. No. 6,117,635), Lux method (U.S. Pat. No. 7,537,886), Plexor method (Sherrill C B, et al., Journal of the American Chemical Society, 126:4550-45569 (2004)), Molecular Beacon method (Tyagi et al, Nature Biotechnology v. 14 Mar. 1996), HyBeacon method (French D J et al., Mol. Cell Probes, 15(6):363-374 (2001)), adjacent hybridization probe method (Bernard, P. S. et al., Anal. Biochem., 273:221 (1999)) and LNA method (U.S. Pat. No. 6,977,295).

Particularly, a duplex is formed by hybridization between an oligonucleotide comprising a hybridizing sequence complementary to the target nucleic acid sequence and a labeled oligonucleotide complementary to at least a portion of the hybridizing sequence.

The duplex may form a duplex in the absence of the target nucleic acid sequence. However, the presence of the target nucleic acid sequence may block the hybridization of the duplex or cause a cleavage of one or more oligonucleotides of the duplex to prevent the formation of the duplex. Therefore, the duplex can provides a signal indicating the presence or absence of the target nucleic acid sequence.

An oligonucleotide comprising a hybridizing sequence complementary to the target nucleic acid sequence may comprise a label and take a role as a detection oligonucleotide.

The duplex between an oligonucleotide comprising a hybridizing sequence complementary to the target nucleic acid sequence and a labeled oligonucleotide complementary to at least a portion of the hybridizing sequence may be generated by various methods, including methods disclosed in Li et al., Nucleic Acids Research, Vol. 30, No. 2, e5 (2002).

Particularly, a duplex is formed in a dependent manner on a mediation oligonucleotide-involving cleavage.

The term used herein "mediation oligonucleotide" is an oligonucleotide which mediates production of a duplex not containing a target nucleic acid sequence.

In an embodiment, a mediation oligonucleotide comprises (i) a targeting portion comprising a hybridizing nucleotide sequence complementary to the target nucleic acid sequence and (ii) a tagging portion comprising a nucleotide sequence non-complementary to the target nucleic acid sequence.

According to an embodiment, the mediation oligonucleotide comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence.

The mediation oligonucleotide may be involved in providing a fragment in various manners.

In an embodiment of the present invention, the mediation oligonucleotide is hybridized with a target nucleic acid sequence and induces a release of a fragment, thereby mediating the production of a duplex.

In an embodiment, a mediation oligonucleotide is hybridized to a target nucleic acid sequence and the mediation oligonucleotide-involving cleavage releases a fragment.

In an embodiment, the mediation oligonucleotide-involving cleavage releases a fragment of the mediation oligonucleotide. Particularly, the fragment of the mediation oligonucleotide comprises at least a portion of a tagging portion of the mediation oligonucleotide.

In an embodiment, a mediation oligonucleotide-involving cleavage releases a fragment of a mediation oligonucleotide-containing amplicon. Particularly, the fragment of the mediation oligonucleotide-containing amplicon comprises a sequence complementary to at least a portion of the tagging portion of the mediation oligonucleotide.

In an embodiment, a mediation oligonucleotide-containing amplicon is produced by amplifying the target nucleic acid sequence using the mediation oligonucleotide as a primer and cleaving a portion of a sequence complementary to the mediation oligonucleotide in the amplicon to release a fragment.

In an embodiment, a primer pair comprising a mediation oligonucleotide as a primer is used for amplifying a target nucleic acid sequence.

In the present invention, a hybridization of mediation oligonucleotide per se does not generate signal and a fragment formed by mediation oligonucleotide-involving cleavage is involved in successive reactions for the formation of duplex.

In an embodiment, the duplex formed in a dependent manner on the mediation oligonucleotide-involving cleavage is a duplex formed in a dependent manner on formation of an extended strand which is formed by extension of a fragment released by the mediation oligonucleotide-involving cleavage.

In an embodiment, a mediation oligonucleotide-involving cleavage releases a fragment and the fragment is specifically hybridized with a capture oligonucleotide and extended on the capturing oligonucleotide to form an extended stand.

In an embodiment, a capturing oligonucleotide comprises in a 3' to 5' direction (i) a capturing portion comprising a nucleotide sequence complementary to the fragment released by the mediation oligonucleotide-involving cleavage and (ii) a templating portion comprising a template sequence for extension reaction.

In an embodiment, a template sequence for extension reaction in the capturing oligonucleotide is determined independent on a target nucleic acid sequence.

In an embodiment, a template sequence for extension reaction in the capturing oligonucleotide is non-complementary to the mediation oligonucleotide.

In an embodiment, the duplex formed in a dependent manner on the mediation oligonucleotide-involving cleavage is a duplex formed by hybridization of a fragment released by the mediation oligonucleotide-involving cleavage with a counterpart oligonucleotide. In this case, there is no extension reaction on the counterpart oligonucleotide.

In an embodiment, the counterpart oligonucleotide has no sequence for extension reaction of the fragment. This method cannot adjust Tm value of a formed duplex by an extension reaction. According to an embodiment, a mediation oligonucleotide-involving cleavage releases a fragment and the fragment is specifically hybridized with a counterpart oligonucleotide.

The mediation oligonucleotide may be hybridized with the counterpart oligonucleotide to form a duplex. However, the cleavage of the mediation oligonucleotide provides a different duplex, i.e. a duplex between the fragment and the counterpart oligonucleotide. A label system may allow the latter duplex to generate a signal indicating the presence or absence of a target nucleic acid sequence by hybridization and/or dissociation of the duplex but the former not to.

In an embodiment, the duplex formed in a dependent manner on the mediation oligonucleotide-involving cleavage is a duplex formed in a dependent manner on formation of an extended strand formed by (i) hybridizing the mediation oligonucleotide with the target nucleic acid sequence, (ii) cleaving the mediation oligonucleotide or the mediation oligonucleotide-containing amplicon by a nuclease to generate a fragment, (iii) hybridizing the fragment with a capturing oligonucleotide comprising a 5'-capturing portion to be hybridized with the fragment and a 3'-templating portion and (iv) performing an extension reaction of the fragment hybridized with the capturing portion on the 3'-templating portion to form the extended strand.

In an embodiment, the mediation oligonucleotide-containing amplicon is cleaved by (i) hybridizing a target nucleic acid sequences with a primer pair comprising an mediation oligonucleotide as a primer (ii) producing a mediation oligonucleotide-containing amplicon and (iii) cleaving a portion of a strand comprising a sequence complementary to the mediation oligonucleotide.

Particularly, the cleaved portion comprises a sequence complementary to at least a portion of a tagging portion of the mediation oligonucleotide wherein the tagging portion comprises a nucleotide sequence non-complementary to the target nucleic acid sequence.

In an embodiment, the duplex formed in a dependent manner on a mediation oligonucleotide-involving cleavage is a duplex formed the duplex formed by (i) hybridizing the mediation oligonucleotide with the target nucleic acid sequence, (ii) cleaving the mediation oligonucleotide by a nuclease to generate a fragment and (iii) hybridizing the fragment with a counterpart oligonucleotide wherein the counterpart oligonucleotide has a sequence complementary to the fragment.

In an embodiment, 5' nuclease or 3' nuclease is used for cleavage of a mediation oligonucleotide. According to an embodiment, a nucleic acid polymerase having 5' nuclease activity or 5' nuclease is used for cleavage of a mediation oligonucleotide.

According to an embodiment, a restriction enzyme is used for cleavage of a mediation oligonucleotide-containing amplicon.

The duplex formed in a dependent manner on formation of the extended strand includes a various type of duplexes. The extended strand itself can form a duplex generating a signal. In addition, the formation of the extended strand can control a formation of other duplexes.

The duplex formed in a dependent manner on formation of the extended strand may be (i) a duplex between the extended strand and the capturing oligonucleotide, (ii) a duplex between the capturing oligonucleotide and a capturing oligonucleotide-hybridizing oligonucleotide, (iii) a duplex between an extended strand-capturing oligonucleotide and a dually extended strand from the extended strand captured to the extended strand-capturing oligonucleotide, (iv) a duplex between the dually extended strand and a dually extended strand-hybridizing oligonucleotide, or (v) a duplex between the extended strand-capturing oligonucleotide and an oligonucleotide to be hybridized with the extended strand-capturing oligonucleotide.

In an embodiment, a mediation oligonucleotide-involving cleavage release a fragment and the fragment is specifically hybridized with a capture oligonucleotide and the fragment is extended to form an extended strand, resulting in formation of an extended duplex between the extended stand and the capture oligonucleotide providing a signal indicating the presence of the target nucleic acid sequence.

In an embodiment, where an extended strand-hybridizing oligonucleotide comprising a hybridizing nucleotide sequence complementary to the extended strand of the fragment is used, the hybridization of the extended strand-hybridizing oligonucleotide and the extended strand forms other type of a duplex providing a signal indicating the presence of the target nucleic acid sequence.

In an embodiment, where a capturing oligonucleotide-hybridizing oligonucleotide comprising a hybridizing nucleotide sequence complementary to the capture oligonucleotide is used, the formation of a duplex between the capturing oligonucleotide-hybridizing oligonucleotide and the capture oligonucleotide is inhibited by the formation of the duplex between the extended strand and the capturing oligonucleotide, thereby providing a signal indicating the presence of the target nucleic acid sequence.

In an embodiment, the extended strand of the fragment is specifically hybridized with an extended strand-capturing oligonucleotide and the extended strand is extended to form an dually extended strand, resulting in formation of a duplex between the dually extended stand and the extended strand-capturing oligonucleotide providing a signal indicating the presence of the target nucleic acid sequence.

In an embodiment, where an dually extended strand-hybridizing oligonucleotide comprising a hybridizing nucleotide sequence complementary to the dually extended strand is used, the hybridization of the dually extended strand-hybridizing oligonucleotide and the dually extended strand forms other type of a duplex providing a signal indicating the presence of the target nucleic acid sequence.

In an embodiment, where an oligonucleotide comprising a hybridizing nucleotide sequence complementary to the extended strand-capturing oligonucleotide is used, the formation of a duplex between the oligonucleotide and the extended strand-capturing oligonucleotide is inhibited by the formation of the duplex between the dually extended strand and the extended strand-capturing oligonucleotide, thereby providing a signal indicating the presence of the target nucleic acid sequence.

In an embodiment, the fragment, the extended strand, the capture oligonucleotide, the extended strand-hybridizing oligonucleotide, capturing oligonucleotide-hybridizing oligonucleotide, the dually extended strand, the extended strand-capturing oligonucleotide, the dually extended strand-hybridizing oligonucleotide, the oligonucleotide comprising a hybridizing nucleotide sequence complementary to the extended strand-capturing oligonucleotide or combination of them can work as the detection oligonucleotide.

The duplex formed in a dependent manner on formation of an extended strand, particularly accompanying the cleavage of the mediation oligonucleotide may be generated by various methods, including PTOCE (PTO cleavage and extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312) and PTOCE-E (PTO Cleavage and Extension-dependent Extension) method (WO2019/066461).

The duplex formed in a dependent manner on formation of an extended strand, particularly accompanying the cleavage of a mediation oligonucleotide-containing amplicon may be generated by various methods, including a method disclosed in W.O. Pub. No. 2017/188669.

With referring to terms disclosed in the above references, the corresponding examples of the oligonucleotides are as follows: a mediation oligonucleotide corresponds to a PTO (Probing and Tagging Oligonucleotide), a capture oligonucleotide to a CTO (Capturing and Templating Oligonucleotide), an extended strand-hybridizing oligonucleotide to a SO (Signaling Oligonucleotide), a capturing oligonucleotide-hybridizing oligonucleotide to a HO (Hybridization Oligonucleotide), a dually extended strand to a second extended strand, an extended strand-capturing oligonucleotide to a second CTO. SOs, HOs, CTOs, extended strands or their combination can play a role as a detection oligonucleotide.

The signal by the duplex formed in a dependent manner on cleavage of the mediation oligonucleotide includes the signal provided by inhibition of the formation of other duplex by the duplex formed in a dependent manner on cleavage of the mediation oligonucleotide (e.g. PCE-NH).

For example, where the signal by the duplex formed in a dependent manner on cleavage of the mediation oligonucleotide is generated by PTOCE method, the signal-generating composition comprises an upstream oligonucleotide and a PTO (Probing and Tagging Oligonucleotide) comprising a hybridizing nucleotide sequence complementary to the target nucleic acid sequence, a CTO (Capturing and Templating Oligonucleotide), suitable label and a template-dependent nucleic acid polymerase having 5' nuclease activity. The PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence. The CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The particular example of the signal generation by PTOCE method comprises the steps of:

(a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; and (d) performing an extension reaction using the resultant of the step (c) and a template-dependent nucleic acid polymerase; wherein the fragment hybridized with the capturing portion of the CTO is extended and an extended duplex is formed; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO; wherein the extended duplex provides a target signal by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) an intercalating label; and (e) detecting the extended duplex by measuring the target signal at a predetermined temperature that the extended duplex maintains its double-stranded form, whereby the presence of the extended duplex indicates the presence of the target nucleic acid sequence. In this case, the method further comprises repeating all or some of the steps (a)-(e) with denaturation between repeating cycles.

In the phrase "denaturation between repeating cycles", the term "denaturation" means to separate a double-stranded nucleic acid molecule to a single-stranded nucleic acid molecule.

In the step (a) of PTOCE method, a primer set for amplification of the target nucleic acid sequence may be used instead of the upstream oligonucleotide. In this case, the method further comprises repeating all or some of the steps (a)-(e) with denaturation between repeating cycles.

The PTOCE method can be classified as a process in which the PTO fragment hybridized with the CTO is extended to form an extended strand and the extended strand is then detected. The PTOCE method is characterized that the formation of the extended strand is detected by using the duplex between the extended strand and the CTO.

There is another approach to detect the formation of the extended strand. For example, the formation of the extended strand may be detected by using an oligonucleotide specifically hybridized with the extended strand (e.g., PCE-SH method). In this method, the signal may be provided from (i) a label linked to the oligonucleotide specifically hybridized with the extended strand, (ii) a label linked to the oligonucleotide specifically hybridized with the extended strand and a label linked to the PTO fragment, (iii) a label linked to the oligonucleotide specifically hybridized with the extended strand and a label incorporated into the extended strand during the extension reaction, or (iv) a label linked to the oligonucleotide specifically hybridized with the extended strand and an intercalating dye. Alternatively, the signal may be provided from (i) a label linked to the extended strand or (ii) an intercalating dye.

Alternatively, the detection of the formation of the extended strand is performed by another method in which inhibition of the hybridization between the CTO and an oligonucleotide being specifically hybridizable with the CTO is detected (e.g. PCE-NH method). Such inhibition is considered to be indicative of the presence of a target nucleic acid sequence. The signal may be provided from (i) a label linked to the oligonucleotide being hybridizable with the CTO, (ii) a label linked to the CTO, (iii) a label linked to the oligonucleotide being hybridizable with the CTO and a label linked to the CTO, or (iv) an intercalating label.

In an embodiment, the oligonucleotide being specifically hybridizable with the CTO has an overlapping sequence with the PTO fragment.

In an embodiment, the detection oligonucleotide includes the oligonucleotide being specifically hybridizable with the extended strand (e.g., PCE-SH method) and oligonucleotide being specifically hybridizable with the CTO (e.g. PCE-NH method). In an embodiment, the detection oligonucleotide includes the extended strand produced during a reaction or CIO.

The PTOCE-based methods commonly involve the formation of the extended strand depending on the presence of a target nucleic acid sequence. The term "PTOCE-based method" is used herein to intend to encompass various methods for providing signals comprising the formation of an extended strand through cleavage and extension of PTO.

The example of signal generation by the PTOCE-based methods comprises the steps of: (a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; (d) performing an extension reaction using the resultant of the step (c) and a template-dependent nucleic acid polymerase; wherein the fragment hybridized with the capturing portion of the CTO is extended to form an extended strand; and (e) detecting the formation of the extended strand by detecting signal generated dependent on the presence of the extended strand. In the step (a), a primer set for amplification of the target nucleic acid sequence may be used instead of the upstream oligonucleotide. In this case, the method further comprises repeating all or some of the steps (a)-(e) with denaturation between repeating cycles.

In an embodiment, the signal generated by the formation of a duplex includes signals induced by hybridization of the duplex (e.g., hybridization of the duplex per se, or hybridization of an extended strand-hybridizing oligonucleotide) or by inhibition of hybridization of a capturing oligonucleotide-hybridizing oligonucleotide due to the formation of a duplex.

In an embodiment, the detection oligonucleotide may be composed of at least one oligonucleotide. In an embodiment, where the detection oligonucleotide is composed of a plurality of oligonucleotides, it may have a label in various manners. For instance, one oligonucleotide among a plurality of oligonucleotides may have at least one label, a plurality of oligonucleotides all may have at least one label, or one portion of oligonucleotides may have at least one label and the other portion may not have a label.

The duplex formed by hybridization of the fragment with a counterpart oligonucleotide may be generated by various methods, including U.S. Pub. No. 2018/0073056.

In an embodiment, duplexes comprise labeled oligonucleotides comprising a label having the same signal property. The term used herein "a label having the same signal property" means that the label has identical or substantially identical signal properties (e.g., optical properties, emission wavelength and electrical signal). For example, FAM and CAL Fluor 610 provide different property of signals (e.g., different emission wavelength ranges) and FAM/Alexa fluor 488, HEX/Alexa fluor 532 and Texas Red/Alexa fluor 594 may be considered to have the same signal property, respectively due to their substantially identical emission wavelengths.

The signals from the duplexes containing a label having the same signal property can be detected by the same detector or the same detection channel. However, the signals cannot be further differentiated which duplexes provide signals in accordance with conventional technologies.

The term used herein "a detector or a detection channel has the same signal property" means that the detector can detect identical or substantially identical signal properties.

The plurality of duplexes have $T_m$ values different from each other. The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$, value may be calculated by conventional methods such as Wallace rule (R. B. Wallace, et al., *Nucleic Acids Research*, 6:3543-3547 (1979)) and nearest-neighbor method (SantaLucia 3. Jr., et al., *Biochemistry*, 35:3555-3562 (1996)); Sugimoto N., et al., *Nucleic Acids Res.*, 24:4501-4505 (1996)).

Tm value of a formed duplex may be obtained empirically using a standard target nucleic acid sequence and a corresponding signal-generating composition. Actual Tm value of a duplex formed in a sample may be measured during the sample analysis.

The label useful in the present invention includes various labels known in the art. For example, the label useful in the present invention includes a single label, an interactive dual label, an intercalating dye and an incorporating label. For example, the label useful in the present invention includes a fluorescent label, a luminescent label, a chemiluminescent label, an electrochemical label and a metal label.

The single label includes, for example, a fluorescent label, a luminescent label, a chemiluminescent label, an electrochemical label and a metal label. In an embodiment, the single label provides a different signal (e.g., different signal intensities) depending on its presence on a double strand or single strand. In an embodiment, the single label is a fluorescent label. The preferable types and binding sites of single fluorescent labels used in this invention are disclosed U.S. Pat. Nos. 7,537,886 and 7,348,141, the teachings of which are incorporated herein by reference in their entity. For example, the single fluorescent label includes JOE, FAM, TAMRA, ROX and fluorescein-based label. The single label may be linked to oligonucleotides by various methods. For instance, the label is linked to probes through a spacer containing carbon atoms (e.g., 3-carbon spacer, 6-carbon spacer or 12-carbon spacer).

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The interactive label system includes a dual label based on "on contact-mediated quenching" (Salvatore et al., Nucleic Acids Research, 2002 (30) no. 21 e122 and Johansson et al., J. AM. CHEM. SOC 2002 (124) pp 6950-6956). The interactive label system includes any label system in which signal change is induced by interaction between at least two molecules (e.g. dye).

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DiIC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable fluorescence molecule and suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent quencher molecule (e.g. black quencher or dark quencher) capable of quenching a fluorescence of a wide range of wavelengths or a specific wavelength may be used in the present invention.

In the signaling system comprising the reporter and quencher molecules, the reporter encompasses a donor of FRET and the quencher encompasses the other partner (acceptor) of FRET. For example, a fluorescein dye is used as the reporter and a rhodamine dye as the quencher.

The interactive dual label may be linked to one strand of a duplex. Where the strand containing the interactive dual label leaves in a single stranded state, it forms a hairpin or random coil structure to induce quenching between the interactive dual label. Where the strand forms a duplex, the quenching is relieved. Alternatively, where the interactive dual label is linked to nucleotides adjacently positioned on the strand, the quenching between the interactive dual label occurs. Where the strand forms a duplex and then is cleaved, the quenching becomes relieved.

Each of the interactive dual label may be linked to each of two strands of the duplex. The formation of the duplex induces quenching and denaturation of the duplex induces unquenching. Alternatively, where one of the two stands is cleaved, the unquenching may be induced.

The incorporating label may be used in a process to generate signals by incorporating a label during primer extension (e.g., Plexor method, Sherrill C B, et al., Journal of the American Chemical Society, 126:4550-45569 (2004)). The incorporating label may be also used in a signal generation by a duplex formed in a dependent manner on cleavage of a mediation oligonucleotide hybridized with the target nucleic acid sequence.

The incorporating label may be generally linked to nucleotides. The nucleotide having a non-natural base may be also used.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner. Specific examples of non-natural bases include the following bases in base pair combinations: iso-C/iso-G, iso-dC/iso-dG, K/X, H/J, and M/N (see U.S. Pat. No. 7,422,850).

Where the signal is generated by the PTOCE method, a nucleotide incorporated during the extension reaction may have a first non-natural base and the CTO may have a nucleotide having a second non-natural base with a specific binding affinity to the first non-natural base.

The term used herein "target nucleic acid", "target nucleic acid sequence" or "target sequence" refers to a nucleic acid sequence of interest for detection or quantification. The target nucleic acid sequence comprises a sequence in a single strand as well as in a double strand. The target nucleic acid sequence comprises a sequence initially present in a nucleic acid sample as well as a sequence newly generated in reactions.

The target nucleic acid sequence may include any DNA (gDNA and cDNA), RNA molecules their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids* Res. 16:10366 (1988)). For reverse transcription, an oligonucleotide dT primer hybridizable to poly A tail of mRNA, random primers or target-specific primers may be used.

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature. The target nucleic acid sequence may include known or unknown sequences.

The term "sample" refers to any material containing or presumed to contain a nucleic acid of interest or which is itself a nucleic acid. More particularly, the term "sample" as used herein includes biological samples (e.g., cells, tissues, and fluid from a biological source) and non-biological samples (e.g., food, water and soil). The biological samples includes, but not limited to, virus, bacteria, tissue, cell, blood, serum, plasma, lymph, sputum, swab, aspirate, bronchoalveolar lavage fluid, milk, urine, feces, ocular fluid, saliva, semen, brain extracts, spinal cord fluid (SCF), appendix, spleen and tonsillar tissue extracts, amniotic fluid and ascitic fluid. The sample can be subjected to pretreatments such as lysis and heating or to nucleic acid extraction process known in the art for efficient amplification reactions (see Sambrook, J. et al., Molecular Cloning, A Laboratory Manual, 3rd ed. Cold Spring Harbor (2001)). The nucleic acid extraction process may vary depending on the type of the sample. Moreover, if the extracted nucleic acid is RNA, a reverse transcription is further performed to synthesize cDNA therefrom (see supra).

A signal-generating composition may include enzymes for the cleavage of oligonucleotides and/or a nucleic acid polymerization such as a 5'-nuclease, a 3'-nuclease, a FEN nuclease, a restriction enzyme, a nucleic acid polymerization and a nucleic acid polymerase having 5'-nuclease activity, a nucleic acid polymerase having 3'-nuclease activity.

Signal-generating compositions for the different target may include common components such a nucleic acid polymerase.

The number of the target nucleic acid sequences to be detected by duplexes including identical signal property of label in a single reaction vessel is including more than 1, 2, 3, 4, 5, 6, 7, 8, 9 and 10 target nucleic acid sequences in the single reaction vessel.

An internal control may be counted as a target nucleic acid sequence detected by the present method.

Unless otherwise indicated, "a plurality of target nucleic acid sequences" in the term used herein "detecting a plurality of target nucleic acid sequences in a sample in a single reaction vessel" may refer to target nucleic acid sequences to be detected by a label having the same signal property. Other target nucleic acid sequences may be present in the identical reaction vessel, which may be detected by different labels having different signal property.

In the single reaction vessel, a plurality of target nucleic acid sequence can be detected by using at least two types of labels each of which has a different signal property. Each label having different signal property can be used to detect one or more target nucleic acid sequences, respectively. In an embodiment, duplexes containing an identical signal property of label have a different Tm value from each other. Signals from labels having different signal property are detected by different detectors, for example, different detection channels.

For example, some duplexes for some target nucleic acid sequences are labeled with FAM and other duplexes for other target nucleic acid sequences with Cal red 610. Two types of detectors (i.e. two detection channels) are used to detect two different emission lights. At least two, three, four, five, six or seven types of labels may be used in a single reaction vessel.

The number of the target nucleic acid sequences to be detected is including more than 1, 2, 3, 4, 5, 6, 7, 8, 9, 10, 15, 18, 20, 25 and 30 target nucleic acid sequences in the single reaction vessel.

Step: Reaction for at Least Two Cycles (120)

A reaction is performed for at least two cycles for (i) the formation of the plurality of duplexes and (ii) a hybridization and/or dissociation of the formed duplexes. The materials of signal-generating compositions may be involved in the reaction to provide corresponding duplexes in dependent manner on the presence or absence of target nucleic acid sequences.

In an embodiment, the reaction is performed under the conditions allowing formation of duplexes and a signal generation from the duplexes. Such conditions include temperatures, salt concentrations and pH of solutions.

In an embodiment of this invention, during the reaction, the number of a duplex for a target nucleic acid sequence increases and the signal intensity from the type of duplex are amplified.

Label position in a duplex may provide different temperature vs signal patterns. For example, where interactive dual label (e.g. a fluorescent report molecule and a quencher molecule) is linked to one strand of a duplex, as a temperature increases, the signal intensity from the group of the duplex may decrease. Alternatively, where one of the fluorescent report molecule and a quencher molecule is linked to one strand and the other label is linked to the other strand of the duplex, the signal intensity from the group of the duplex may increase with temperature.

The reaction of the present method may refer to "signal-generating process". The term used herein "signal-generating process" refers to any process capable of generating signals in a dependent manner on the presence or absence of a target nucleic acid sequence in a sample.

The signal-generating process is accompanied with signal change. The term "signal" as used herein refers to a measurable output.

The progress of the signal-generating reaction is evaluated by measuring the signal. A signal value or signal change may serve as an indicator indicating a property of the target analyte, in particular qualitatively or quantitatively the presence or absence of the target analyte. The signal change may comprise a signal decrease as well as a signal increase.

Examples of useful indicators include fluorescence intensity, luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The most widely used indicator is fluorescence intensity.

The term used herein "signal generation" include appearance or disappearance of signals and increase or decrease in signals. Particularly, the term "signal generation" means increase in signals.

In an embodiment, the signal-generating process is a signal amplification process.

The term used herein "amplification reaction" refers to a reaction for increasing or decreasing signals.

In an embodiment, the amplification reaction refers to an increase (or amplification) of a signal generated depending on the presence of the target nucleic acid sequence by using the signal-generating composition. In an embodiment, the amplification reaction refers to an increase (or amplification) of signal by increase of the number of a duplex for the corresponding target nucleic acid sequence. The amplification reaction is accompanied with or without an amplification of the target nucleic acid sequence. More particularly, the amplification reaction of the present invention refers to a signal amplification reaction performed with an amplification of target nucleic acid sequence.

The data set obtained from an amplification reaction comprises an amplification cycle or cycle number.

The term used herein "cycle" refers to a unit of changes of conditions in a plurality of measurements accompanied with changes of conditions. For example, the changes of conditions refer to an increase or decrease of temperature, reaction time, reaction number, concentration, pH and/or replication number of a measured subject (e.g., target nucleic acid molecule). Therefore, the cycle may refer to a time or a process cycle, a unit operation cycle and a reproductive cycle.

For another example, when an isothermal amplification of nucleic acid is performed, the signals of a single sample are measured multiple times with a regular interval of times under isothermal conditions. In this reaction, the reaction time may correspond to the changes of conditions and a unit of the reaction time may correspond to a cycle.

Particularly, when repeating a series of reactions or repeating a reaction with a time interval, the term "cycle" refers to a unit of the repetition.

For example, in a polymerase chain reaction (PCR), a cycle refers to a reaction unit comprising denaturation of a target nucleic acid molecule, annealing (hybridization) between the target nucleic acid molecule and primers and primer extension. The increases in the repetition of reactions may correspond to the changes of conditions and a unit of the repetition may correspond to a cycle.

A data set obtained from a signal-generating process comprises a plurality of data points comprising cycle numbers and signal values.

In an embodiment, the amplification reaction to amplify signals indicative of the presence of the target nucleic acid molecule is performed in such a manner that signals are amplified simultaneously with amplification of the target nucleic acid molecule (e.g., real-time PCR). Alternatively, the amplification reaction is performed in such a manner that signals are amplified with no amplification of the target nucleic acid molecule.

In the present invention, the number of a duplex generating a signal may be may be amplified simultaneously with target amplification. Alternatively, the number of a duplex generating a signal may be amplified with no target amplification.

In an embodiment, the signal-generating composition comprises at least one primer pair for amplifying the plurality of target nucleic acid sequences and the duplex reaction is accompanied by amplification of the plurality of target nucleic acid sequences.

Target nucleic acid sequences may be amplified by various methods. For example, a multitude of methods have been known for amplification of a target analyte, including, but not limited to, PCR (polymerase chain reaction), LCR (ligase chain reaction, see U.S. Pat. No. 4,683,195 and No. 4683202; PCR Protocols: A Guide to Methods and Applications (Innis et al., eds, 1990)), SDA (strand displacement amplification) (Walker, et al. Nucleic Acids Res. 20(7): 1691-6 (1992); Walker P C R Methods Appl 3(1):1-6 (1993)), transcription-mediated amplification (Phyffer, et al., J. Clin. Microbiol. 34:834-841 (1996); Vuorinen, et al., J. Clin. Microbiol. 33:1856-1859 (1995)), NASBA (nucleic acid sequence-based amplification, see Compton, J. Nature 350(6313):91-2 (1991)), rolling circle amplification, RCA) (Lisby, Mol. Biotechnol. 12(1):75-99 (1999); Hatch et al., Genet. Anal. 15(2):35-40 (1999)), or Q-beta (Q-Beta Replicase) (Lizardi et al., BioITechnology 6:1197 (1988)).

In an embodiment, the amplification reaction may amplify signals simultaneously with amplification of the target analyte, particularly the target nucleic acid molecule. In an embodiment, the amplification reaction is performed in accordance with a PCR or a real-time PCR.

In an embodiment of the present invention, a nucleic acid polymerase having a nuclease activity (e.g. 5' nuclease activity or 3' nuclease activity) may be used for amplification of target nucleic acid sequences. In an embodiment, a nucleic acid polymerase having a no nuclease activity may be used for amplification of target nucleic acid sequences.

The nucleic acid polymerase useful in the present invention is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophllus*, *Thermus chliarophilus*, *Thermus flavus*, *Thermus igniterrae*, *Thermus lacteus*, *Thermus oshimai*, *Thermus ruber; Thermus rubens*, *Thermus scotoductus*, *Thermus silvanus*, *Thermus* species Z05, *Thermus* species sps 17, *Thermus thermophllus*, *Thermotoga maritime*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosipho africanus*, *Pyrococcus woesei*, *Pyrococcus horikoshii*, *Pyrococcus abyssi*, *Pyrodictium occultum*, *Aquifex pyrophilus* and *Aquifex aeolieus*. Particularly, the thermostable DNA polymerase is Taq polymerase.

In an embodiment, the amplification of the target nucleic acid sequence is accomplished by an asymmetric PCR. The ratio of primers may be selected in consideration of cleavage or hybridization of downstream oligonucleotides.

In an embodiment, a reaction is performed for at least 2 cycles, at least 5 cycles, at least 10 cycles, at least 20 cycles, at least 30 cycles, at least 40 cycles, at least 45 cycles or at least 50 cycles. In an embodiment, a reaction is performed for at most 100 cycles, at most 90 cycles, at most 80 cycles, at most 70 cycles or at most 60 cycles.

Step: Obtaining Signal Values (130)

Signal values are obtained at all or partial cycles of the reaction at at least two detection temperatures in each of a plurality of detection temperature ranges assigned to the plurality of target nucleic acid sequences. Each of the plurality of detection temperature ranges comprises a temperature range in which the amount of a duplex for each corresponding target nucleic acid sequence is changed.

During the reaction, signals may be measured at a plurality of detection temperatures.

The at least two detection temperatures are used for detection of a single target nucleic acid sequence.

For each target nucleic acid sequence, the at least two detection temperatures at which the signal values are to be obtained may be predetermined from each detection temperature range.

As one example, the at least two detection temperatures may be determined for each target nucleic acid sequence and then combined to finally determine all detection temperatures for the entire reaction. As another example, all detection temperatures for the entire reaction may be determined and then assigned to the at least two detection temperatures for each target nucleic acid sequence.

The detection temperature range for each target nucleic acid sequence may be a temperature range from which the at least two detection temperatures for a corresponding target nucleic acid sequence are selected. Alternatively, the detection temperature range may be one which is formed or positioned by the at least two detection temperatures assigned to each target nucleic acid sequence.

In one embodiment, the detection temperature range assigned to each target nucleic acid sequence is subject to the requirements.

In one embodiment of the invention, the at least two detection temperatures for each target nucleic acid sequence are determined such that they satisfy the requirements for the at least detection temperatures as well as the requirements for the detection temperature range.

The at least two detection temperatures for each target nucleic acid sequence (or the detection temperature range for each target nucleic acid sequence) may be selected in consideration of the change in signal value with temperatures, for a duplex derived from each target nucleic acid sequence.

Temperatures affecting the hybridization/dissociation of a duplex may be divided as follow: (i) a temperature range in which the duplex is in a hybridized state; (ii) a temperature range in which the duplex is changing from a hybridized state to a dissociated state (i.e., a temperature range where the dissociation of the duplex occurs or the hybridization of the duplex occurs, and (iii) a temperature range in which the duplex is in a dissociated state.

The morphology of the duplex in such temperature ranges is intended to indicate the probabilistic dominance thereof, but is not absolutely limited to that morphology.

When a plurality of the duplexes is present, most of the duplexes are in a hybridized state at any temperature below the temperature range in which the duplex is changing from a hybridized state to a dissociated state (i.e., the temperature range where the dissociation occurs), thereby causing no substantial change in the amount of the duplexes; Most of the duplexes are in dissociated state at any temperature above the temperature range in which the duplex is changing from a hybridized state to a dissociated state (i.e., the temperature range where the dissociation occurs), thereby causing no substantial change in the amount of duplexes. On the other hand, for the temperature range in which the duplex is changing from a hybridized state to a dissociated state (i.e., the temperature range where the dissociation occurs), more dissociation takes place at higher temperatures, thereby causing a change in the amount of duplexes with temperatures.

As used herein, the term "a [the] temperature range in which the amount of a duplex is not substantially changed" refers to a temperature range in which the change in the amount of a duplex per unit temperature within the temperature range is no more than 10%, 8%, 6%, 5%, 4%, 3%, 2%, or 1%.

As used herein, the term "an [the] amount of a duplex" refers to the quantity or number of two strands hybridized to each other, which constitute a duplex.

When the duplex provides a signal value depending on the formation of the duplex, the duplex can provide a melt curve showing the change in signal value with temperatures.

Figure 2:
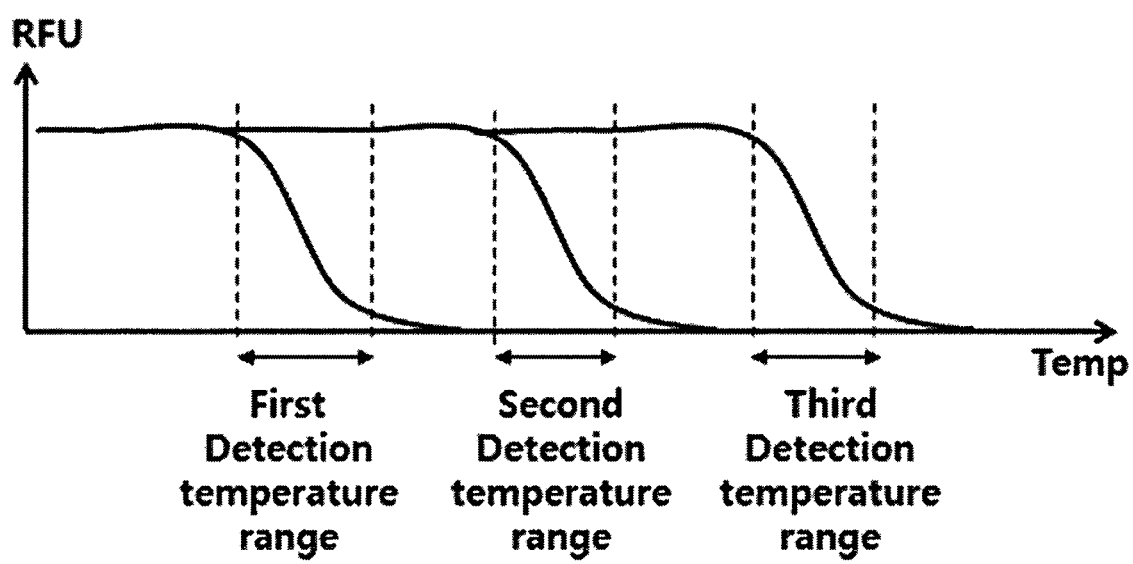
FIG. 2 illustrates an embodiment of three detection temperature ranges for three target nucleic acid sequences.

FIG. 2 shows the melt curves of three duplexes with different Tm values.

In FIG. 2, the duplexes show a pattern in which the signal decreases as the temperature increases. In FIG. 2, each of the duplexes has a label such that it provides a signal upon hybridization of two strands thereof and does not provide a signal upon dissociation of two strands thereof. For example, each of the duplexes has an interactive dual label linked to either strand thereof. If each of the duplexes has a label such that it does not provide a signal upon hybridization of two strands thereof but provides a signal upon dissociation of two strands thereof, the signal increases as the temperature increases.

In an embodiment of the present invention, the detection temperature range (see FIG. 2; first detection temperature range, second detection temperature range, or third detection temperature range) comprises a temperature range in which the amount of a duplex for each corresponding target nucleic acid sequence is changed.

In an embodiment, at least one detection temperature for each corresponding target nucleic acid sequence falls within a temperature range in which the amount of a duplex for each corresponding target nucleic acid sequence is changed.

All or part of the temperature range in which the dissociation of the duplex occurs may be the temperature range in which the amount of a duplex for each corresponding target nucleic acid sequence is changed.

In an embodiment, the detection temperature range may further comprise a temperature range in which the amount of a duplex for the corresponding target nucleic acid sequence remains unchanged. For example, the detection temperature range is a temperature range in which most of the duplexes for the corresponding target nucleic acid sequence are in a hybridized state or in a dissociated state. In one embodiment, at least one detection temperature for the corresponding target nucleic acid sequence falls within a temperature range in which most of the duplexes are in a hybridized state or in a dissociated state.

In an embodiment, the detection temperature range is a temperature range in which the amount of a duplex for the corresponding target nucleic acid sequence is changed but the amount of duplexes for other target nucleic acid sequences remains unchanged.

FIG. 2 illustrates three detection temperature ranges for three target nucleic acid sequences. Each of the plurality of detection temperature ranges corresponds to each of the plurality of target nucleic acid sequences. For example, the first detection temperature range is a temperature range for detecting the first target nucleic acid sequence, the second detection temperature range for detecting the second target nucleic acid sequence, and the third detection temperature range for the third target nucleic acid sequence.

In FIG. 2, the first detection temperature range is a temperature range in which the amount of a duplex for the first target nucleic acid sequence is changed, the second detection temperature range is a temperature range in which the amount of a duplex for the second target nucleic acid sequence is changed, and the third detection temperature range is a temperature range in which the amount of a duplex for the third target nucleic acid sequence is changed. Particularly, each of the detection temperature ranges is a temperature range in which the amount of duplexes for other target nucleic acid sequences remains unchanged.

As used herein, the expression "a [the] temperature range in which the amount of a duplex for the corresponding target nucleic acid sequence is changed but the amount of duplexes for other target nucleic acid sequences remains unchanged" is intended to encompass a temperature range in which the amount of duplexes for other target nucleic acid sequences is not changed at all, as well as a temperature range in which the amount of duplexes for other target nucleic acid sequences is very little changed. In an embodiment, each of the plurality of detection temperature ranges is selected from a temperature range in which the ratio of the change amount of signal generated by the duplexes for other target nucleic acid sequence to the change amount of signal generated by the duplex for the corresponding target nucleic acid sequence is no more than 10%, 9%, 8%, 7%, 6%, 5%, 4%, 2%, or 1%.

For example, in the case of the presence of a first target nucleic acid sequence, a second target nucleic acid sequence and a third target nucleic acid sequence in a sample, the first detection temperature range is a temperature range in which the signal for the first target nucleic acid sequence is changed but the signals for the second and the third target nucleic acid sequences remain substantially unchanged. The second detection temperature range is a temperature range in which the signal for the second target nucleic acid sequence is changed but the signals for the first and the third target nucleic acid sequences remain substantially unchanged. The third detection temperature range is a range in which the signal for the third target nucleic acid sequence is changed but the signals for the first and the second target nucleic acid sequences remain substantially unchanged.

According to one embodiment, the detection temperature range for a target nucleic acid sequence may comprise a limited portion of a temperature range in which the amount of duplexes for other target nucleic acid sequences is changed. For example, the change amount of signals generated by the duplexes for other target nucleic acid sequences in the overlapped temperature range may be no more than 20%, 15%, 10%, 9%, 8%, 7%, 6%, 5%, 4%, 3%, 2%, or 1% of the total change amount of signals generated. For example, a temperature range for a target nucleic acid sequence may overlap with the temperature ranges for other target nucleic acid sequences by 10° C., 5° C., 4° C., 3° C., 2.5° C., 2° C., 1.5° C., or 1° C.

In an embodiment, the detection temperature range comprises a temperature range in which the amount of a duplex for the corresponding target nucleic acid sequence is changed and does not comprise or comprise a portion of a temperature range in which the amount of other duplexes is changed.

In an embodiment, the detection temperature range for each of the target nucleic acid sequences can be determined so as not to overlap with the detection temperature ranges for other target nucleic acid sequences.

The large difference in $T_m$ values between different duplexes can allow the detection temperature ranges not to overlap with each other. Even when the difference in $T_m$ values between the different duplexes is small, the detection temperature ranges may not be overlapped with each other by adjustment of the number or the spacing of the detection temperatures.

In an embodiment, the detection temperature range for the corresponding target nucleic acid sequence may overlap with the detection temperature ranges for other target nucleic acid sequences. In particular, the overlapping temperature range is no more than 10° C., 5° C., 4° C., 3° C., 2.5° C., 2° C., 1.5° C., or 1° C.

In an embodiment, the plurality of signal-generating compositions are designed such that the $T_m$'s of the duplexes provided by signal-generating compositions are sufficiently spaced from each other in order to prevent the temperature ranges in which the amount of a duplex for each of the plurality of target nucleic acid sequences remains unchanged from overlapping with each other. If there is an overlap between some of the temperature ranges in which the amount of a duplex for each of the plurality of target nucleic acid sequences is changed, the detection temperature ranges are set to minimize its overlap.

In an embodiment, each of the detection temperature ranges is set to cover the expected $T_m$ value of a duplex for the corresponding target nucleic acid sequence.

In an embodiment, the detection temperature range for each of the target nucleic acid sequences is within 20° C., 15° C., 10° C., 6° C., 5° C., 4° C., or 3° C.

In an embodiment, the detection temperature range may be represented by the range between a highest detection temperature and a lowest detection temperature.

In an embodiment, the detection temperature range for each of the target nucleic acid sequences is within $T_m \pm 10°$ C., $T_m \pm 8°$ C., $T_m \pm 5°$ C., $T_m \pm 3°$ C., $T_m \pm 2°$ C., $T_m \pm 1.5°$ C., or $T_m \pm 1°$ C., wherein Tm indicates a $T_m$ value of the corresponding duplex.

The signal values are obtained at least two detection temperatures for each target nucleic acid sequence.

In an embodiment, the signal values are obtained at two detection temperatures within the detection temperature range assigned to each target nucleic acid sequence.

In an alternative embodiment, the signal values are obtained at three or more detection temperatures within the detection temperature range assigned to each target nucleic acid sequence.

In a particular embodiment of the present invention, the signal values are obtained at three (3), four (4), five (5), six (6), seven (7), eight (8), nine (9) or ten (10) detection temperatures within the detection temperature range assigned to each target nucleic acid sequence.

In an embodiment, the signal values are obtained at no less than two, three, five, ten, fifteen detection temperatures within a detection temperature range assigned to each target nucleic acid sequence.

In an embodiment, the signal values are obtained at no more than 100, 70, 50, 40, 30, 20, or 10 temperatures within the detection temperature range assigned to each target nucleic acid sequence.

In an embodiment, two or more of the detection temperatures for each target nucleic acid sequence are detection temperatures at which the corresponding duplex provides substantially different signal values. For example, when using two detection temperatures, the two detection temperatures are spaced from each other such that the corresponding duplex provides different signal values at the two detection temperatures. For example, the two detection temperatures are spaced from each other by no more than 0.1° C., 0.2° C., 0.5° C., or 1° C. Alternatively, the two detection temperatures are not selected from a temperature range in which the duplex is in a hybridized state, or the two detection temperatures are not selected from a temperature range in which the duplex is in a dissociated state.

In an embodiment, the at least two detection temperatures for each target nucleic acid sequence are detection temperatures at which the corresponding duplex provides substantially different signal values.

In an embodiment, the at least two detection temperatures for each target nucleic acid sequence comprise at least two temperatures selected from a temperature range in which the amount of a duplex for the corresponding target nucleic acid is changed.

Figure 3:
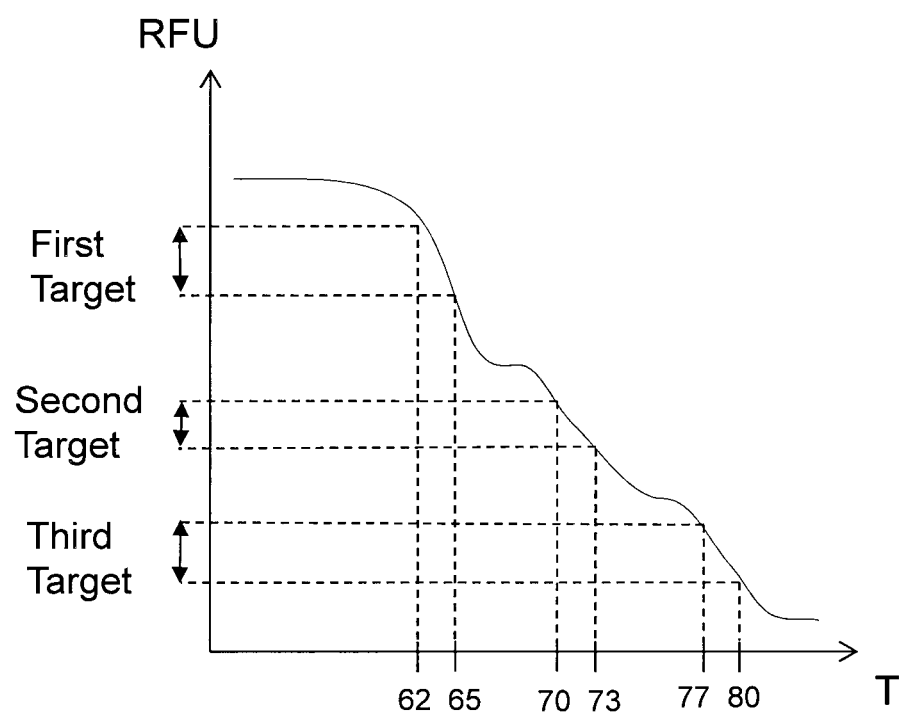
FIG. 3 illustrates an embodiment of signal-change values calculated by signal values at the tow reference detection temperatures for each of three target nucleic acid sequences.

FIG. 3 illustrates the selection of two detection temperatures from a temperature range in which the amount of the corresponding duplex is changed.

In one embodiment, some of the at least two detection temperatures for each target nucleic acid sequence are selected from a temperature range in which the amount of a duplex for the corresponding target nucleic acid sequence is changed, and the remainder is selected from a temperature range in which the amount of a duplex for the target nucleic acid sequence remains unchanged.

In an embodiment, some of the at least two detection temperatures for each target nucleic acid sequence may be selected from a temperature range in which the duplex is in a hybridized state and the others may be selected from a temperature range in which the duplex is in a dissociated state.

In an embodiment, the at least two detection temperatures are selected such that an expected Tm value of the duplex for each corresponding nucleic acid sequence is encompassed between a highest detection temperature and a lowest detection temperature of the at least two detection temperatures.

In an embodiment, the spacing of detection temperatures for each target nucleic acid sequence is no more than 5° C., 4° C., 3° C., 2.5° C., 2° C., 1.5° C., 1° C., 0.5° C., or 0.1° C.

In an embodiment, the at least two detection temperatures comprises a highest detection temperature and a lowest detection temperature between which difference is no more than 20° C., no more than 15° C., no more than 10° C., no more than 8° C., no more than 7° C., no more than 6° C., no more than 5° C., no more than 4° C. or no more than 3° C.

In an embodiment, the at least two detection temperatures for each target nucleic acid sequence are within $T_m \pm 10°$ C., $T_m \pm 8°$ C., $T_m \pm 5°$ C., $T_m$ f 2° C., or $T_m$ 1.5° C., wherein $T_m$ indicates a $T_m$ value of the corresponding duplex.

In an embodiment, some of the detection temperatures for different target nucleic acid sequences may overlap. In particular, in the case of selecting two of the plurality of detected temperatures as the reference temperatures in accordance with the present method, an overlap may occur between the detection temperatures.

In an embodiment, the number of overlapping detection temperatures for two different target nucleic acid sequences may be one (1), two (2), three (3), four (4), or five (5).

In an embodiment, at least two of the detection temperatures for each target nucleic acid sequence do not overlap with the detection temperatures for other target nucleic acid sequences.

In an embodiment, the signal values are detected at all or partial cycles. For example, for a total of 45 cycles performed, signal values can be detected at all cycles from $1^{st}$ cycle to $45^{th}$ cycle.

In an embodiment, the signal values may be obtained at odd-numbered cycles. For example, for a total of 45 cycles performed, signal values may be detected at $1^{st}$, $3^{rd}$, $5^{th}$, $7^{th}$ ... $45^{th}$ cycle.

In an embodiment, the signal values may be obtained in even-numbered cycles. For example, for a total of 45 cycles performed, signal values may be detected at $2^{nd}$, $4^{th}$, $6^{th}$, $8^{th}$ ... $44^{th}$ cycle. Further, signal values may be additionally detected at $45^{th}$ cycle, considering $45^{th}$ cycle is the end cycle in the reaction.

In an embodiment, the signal values may be obtained at one or more cycles predetermined by a user. For example, one or more cycles at which signal values are to be detected can be determined before performing the one or more cycles of reaction. For example, cycles from $10^{th}$ cycle to $45^{th}$ cycle may be predetermined, or cycles from $10^{th}$ cycle to $40^{th}$ cycle may be predetermined. The predetermined cycles may be consecutive or non-consecutive, and may be at regular or irregular intervals. In an embodiment, the signal values may not be obtained at early cycles. For example, the early cycles may be from $1^{st}$ cycle to $5^{th}$ cycle. Since low intensity of signals may be detected at the early cycles but the signal-change value is not expected to be significant, the gratuitous detection at the early cycles can be omitted. Such omission of the detection of signal values at the early cycles can reduce the overall time of the reaction cycles.

In one embodiment, the signal values obtained at the at least two detection temperatures may be subjected to interpolation to yield an expected signal value at another temperature. The expected signal value obtained by interpolation can be referred to as "interpolated signal value", and the corresponding detection temperature can be referred to as "interpolated temperature" or "interpolated detection temperature".

In one embodiment of the invention, the interpolated temperature is any temperature between the detection temperatures.

In one embodiment of the invention, the signal values obtained at a cycle may be subjected to interpolation to yield an expected signal value at another cycle. The cycle having the expected signal value obtained by interpolation can be referred to as "interpolated cycle".

The interpolation can be performed by linear interpolation, double linear interpolation, parabolic interpolation, polynomial interpolation, or spline interpolation, and more particularly linear interpolation.

Unless otherwise indicated, the term used herein "detection temperature" encompasses detection temperatures generated by interpolation as well as detection temperatures at which a signal is measured instrumentally.

Unless otherwise indicated, the term used herein "signal value" encompasses signal values generated by interpolation as well as signal values obtained by instrumental measuring.

In one embodiment of the invention, when temperatures and signal values thereof are interpolated from the at least two detection temperatures, the at least two detection temperatures comprise the interpolated detection temperatures.

As used herein, the term "signal value" refers to either a signal value actually measured at a cycle of the signal-generating reaction, particularly the amplification reaction or its modification, which is quantified on a certain scale. The modification may comprise a mathematically processed value of actually measured signal value. Examples of mathematically processed value of actually measured signal value (i.e., signal value of a raw dataset) may include, but are not limited to, a logarithmic value of the measured signal value; or a derivative of the measured signal value Step: Obtaining a Data Set of Cycle/Signal-Change Value (140)

A signal-change value of signal values between two reference temperatures selected from the at least two detection temperatures in each of the plurality of detection temperature ranges is obtained such that a data set of cycle/signal-change value for each of the plurality of target nucleic acid sequences is obtained.

Selection of Reference Temperatures

The reference temperatures are selected from the at least two detection temperatures in each of the plurality of detection temperature ranges.

The reference temperatures to be selected from the at least two detection temperatures may be predetermined. Alternatively, the reference temperatures may be selected from the at least two detection temperatures by analyzing the signal values obtained at the detection temperatures.

As used herein, the term "selection of reference temperatures" encompasses selecting predetermined reference temperatures from the at least two detection temperatures as well as selecting reference temperatures from the at least two detection temperatures based on certain criteria in the performance of the method.

In one embodiment, if there are two detection temperatures in the detection temperature range for each target nucleic acid sequence, the two detection temperatures are selected as the two reference temperatures.

In one embodiment, if there are three or more detection temperatures in the detection temperature range for each target nucleic acid sequence, two of the three or more detection temperatures are selected as the reference temperatures.

In one embodiment, if there are there or more detection temperatures in the detection temperature range for each target nucleic acid sequence, a lowest detection temperature and a highest detection temperature are selected as the two reference temperatures.

In one embodiment, the signal values at any temperature between the two reference temperatures may also be employed to generate a signal-change value using the reference temperatures.

In one embodiment, if there are there or more detection temperatures in the detection temperature range for each target nucleic acid sequence and the detection temperatures include an interpolated detection temperature(s), the reference temperatures are selected from (i) the detection temperatures, (ii) the interpolated temperatures, or (iii) the detection temperatures and the interpolated detection temperature(s).

In one embodiment of the invention, the two reference temperatures for the plurality of target nucleic acid sequence are not overlapped with each other. In other word those, the two reference temperatures for the plurality of target nucleic acid sequence may be not overlapped each other. In one embodiment of the invention, the two reference temperatures for a target nucleic acid sequences do not overlap with other reference temperatures for other target nucleic acid sequences. The two reference temperatures for each target nucleic acid sequence may be selected so as not to overlap with each other, because they are used to obtain a signal-change value for determining the presence or absence of the corresponding target nucleic acid sequence.

In one embodiment of the invention, the two reference temperatures for a target nucleic acid sequence are different from those for other target nucleic acid sequence. In one embodiment, the two reference temperatures for a target nucleic acid sequence fall within a temperature range in which the amount of a duplex for the corresponding target nucleic acid sequence is changed.

In one embodiment, the two reference temperatures for a target nucleic acid sequence are selected to be spaced at regular intervals. For example, the two reference temperatures is spaced to be 5° C., 4° C., 3° C., 2° C., or 1° C.

In one embodiment, the two reference temperatures for a target nucleic acid sequence are selected to be spaced at regular intervals around the $T_m$ of a duplex.

In one embodiment, the two reference temperatures for each target nucleic acid sequence are selected to be spaced at regular intervals around the $T_m$ of a duplex for the corresponding target nucleic acid sequence. In this case, the Ct values obtained by applying an identical threshold value to data sets of cycle/signal-change value may be compared with each other.

On the other hand, when analyzing an unknown sample, a real reaction $T_m$ value of a duplex for a target nucleic acid sequence in a sample may differ from an expected $T_m$ value, depending on the components contained in the sample or the experimental conditions. In this case, the selection of two reference temperatures based on the expected $T_m$ may cause inaccuracy of the method. The present invention allows measurement of signal values at a plurality of detection temperatures for each target nucleic acid sequence and selection of two suitable reference temperatures from the plurality of detection temperatures.

The selection of two reference temperatures from a plurality of detection temperatures for each target nucleic acid sequence can be performed by various methods.

In an embodiment, the at least two detection temperatures is no less than 3 in number; the method further comprises analyzing the signal values at the least three detection temperatures to select the two reference temperatures.

The reference temperatures may be selected based on signal values at a plurality of detected temperatures.

In an embodiment, the at least two detection temperatures is no less than 3 in number; signal-change values are calculated by using signal values at the at least three detection temperatures to select the two reference temperatures.

In an embodiment, the at least two detection temperatures is no less than 3 in number; signal-change values are calculated by using signal values at the at least three detection temperatures and the two reference temperatures are selected such that a highest signal-change value among the calculated signal-change values is included between the two reference temperatures.

In an embodiment, signal-change values are assigned with temperatures between the detection temperatures used for calculating the corresponding signal-change value.

In an embodiment, the highest signal-change value is assigned with a temperature between the detection temperatures used for calculating the highest signal-change value.

For example, signal-changes values are calculated by using signal values between immediately adjacent detection temperatures, and the two reference temperatures are selected such that a highest signal-change value among the calculated signal-change values is included between the two reference temperatures.

Figure 4:
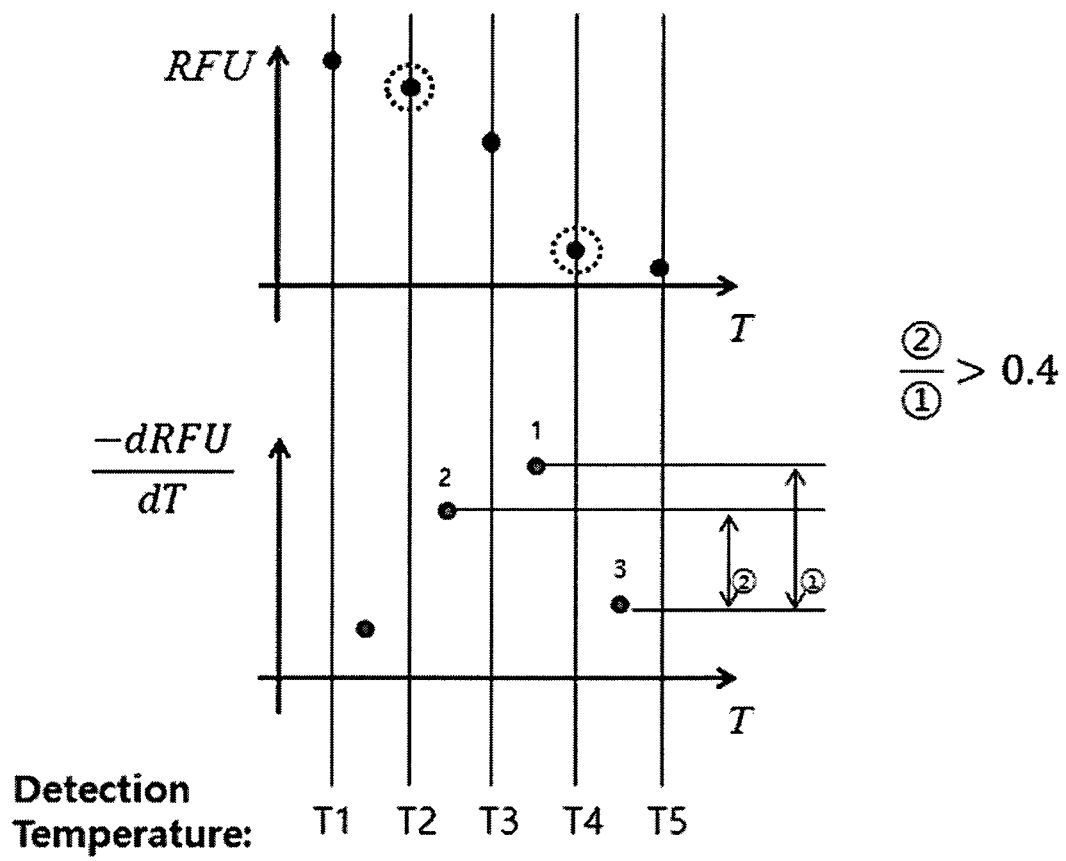
FIG. 4 illustrates an embodiment of selecting two reference temperatures from a plurality of detection temperatures.

FIG. 4 illustrates selecting two reference temperatures in accordance with one embodiment of the present invention. In particular, FIG. 4 depicts a process of selecting two reference temperatures based on signal-change values calculated from signal values between immediately adjacent detection temperatures.

FIG. 4 shows an example of selecting T2 and T4 as reference temperatures.

In one example, the signal values at at least one cycle are used for selection of the reference temperatures. The signal values at 1-80 cycles, 1-50 cycles, 1-30 cycles, 5-80 cycles, 5-50 cycles and 5-30 cycles are used for selection of the reference temperatures.

In one example, the signal values at the end cycle are used for selection of the reference temperatures. For example, if the end cycle is $45^{th}$ cycle, the signal values detected at $45^{th}$ cycle may be used to select the reference temperatures. In one example, the signal values at the late cycles are used for selection of the reference temperatures. For example, if the end cycle is $45^{th}$ cycle, the signal values detected at $41^{th}$ to $45^{th}$ cycles (5 cycles) may be used to select the reference temperatures. The late cycles consist of the end cycle and the cycles adjacent to (around) the end cycle.

FIG. 4 exemplifies selection of reference temperatures based on the signal values at one cycle. When reference temperatures are selected based on the signal values at the late cycles (at least two cycles), the reference temperatures may be selected based on the average of the signal change values calculated at the late cycle. In other words, the signal-change values are firstly calculated at each cycle, and the average of the signal-change values at the same temperature is then calculated to generate the averaged signal-change values. Once the averaged signal-change values are generated, the reference temperatures are selected based on the magnitude of the averaged signal-change value.

In another example, reference temperatures may be selected based on the averaged signal-change values calculated from the averaged signal values at the late cycles. The average of the signal values at the same temperature at the late cycles is calculated to generate the averaged signal values and then a change value of the averaged signal values is calculated to generate the averaged signal-change value.

A signal-change value may be calculated from the signal values at two consecutive detection temperatures. Once the signal values are obtained at five detection temperatures at one cycle, four signal change values are calculated from the values. The temperatures corresponding to the four signal change values may be considered as interpolated temperatures between two consecutive detection temperatures. The signal-change values may be calculated by the difference in the signal values relative to the difference in the detected temperatures.

Once the signal change values are calculated, the reference temperatures may be selected based on the magnitude of the signal change values. In one example, reference temperatures may be selected to comprise a highest signal-change value. The reference temperatures may be selected to comprise a highest signal change value and either of the two signal change values adjacent to the highest signal change value, wherein the either of the two signal change values adjacent to the highest signal change value are comprised as the reference temperature by calculation of the difference between any two signal change values among the highest signal change value and two adjacent signal change values.

In an embodiment, the signal-change values are assigned at temperatures between the detection temperatures used for calculating corresponding signal-change values; the highest signal-change value among the signal-change values is assigned as a first-change value, a higher signal-change value and a lower signal-change value among two signal-change values adjacent to the highest signal-change value are assigned as a second signal-change value and a third signal-change value, respectively; if the ratio of (i) difference between the second signal-change value and the third signal-change value to (ii) difference between the first signal-change value and the third signal-change value exceeds a threshold value, the highest signal-change value is assigned at a median temperature between the temperature for the first signal-change value and the temperature for the second signal-change value, and two temperatures being apart from the median temperature are selected as the two reference temperatures.

In an embodiment, two temperatures being apart from the median temperature in the same interval are selected in both directions as the two reference temperatures.

FIG. 4 depicts an example in which the ratio of the difference between the second signal change value and the third signal change value to the difference between the first signal change value and the third signal change value exceeds a threshold value of 0.4. The threshold value may be set to a value of no less than 0.2, 0.3, 0.4, 0.5, or 0.6.

As shown in FIG. 4, since the ratio exceeds the threshold value, the highest signal-change value is assigned at a median temperature between the temperature for the first signal-change value and the temperature for the second signal-change value and the temperatures T2 and T4 being apart from the median temperature in the same interval are selected in both directions as the two reference temperatures.

Figure 5:
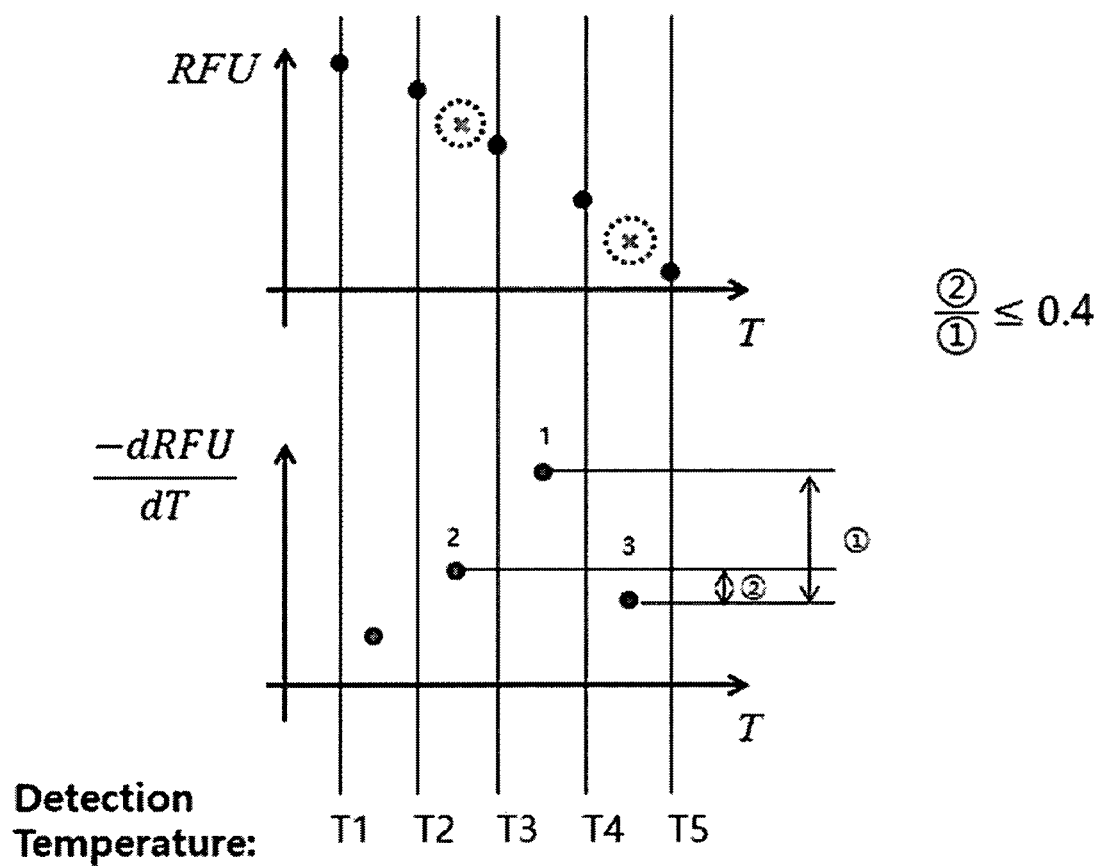
FIG. 5 illustrates another embodiment of selecting two reference temperatures from a plurality of detection temperatures.

FIG. 5 illustrates selecting reference temperatures in accordance with another embodiment of the present invention.

In an embodiment, the signal-change values are assigned at temperatures between the detection temperatures used for calculating corresponding signal-change values; a highest signal-change value among the signal-change values is assigned as a first-change value, a higher signal-change value and a lower signal-change value among two signal-change values adjacent to the highest signal-change value are assigned as a second signal-change value and a third signal-change value, respectively; if the ratio of (i) difference between the first signal-change value and the third signal-change value to (ii) difference between the second signal-change value and the third signal-change value is no more than a threshold value, the highest signal-change value is assigned at the temperature for the first signal-change value and two temperatures being apart from the temperature for the first signal-change value are selected as the two reference temperatures.

In an embodiment, two temperatures being apart from the temperature for the first signal-change value in the same interval are selected in both directions as the two reference temperatures.

FIG. 5 depicts an example in which the ratio of the difference between the second signal change value and the third signal change value to the difference between the first signal change value and the third signal change value no more than a threshold value of 0.4. As shown in FIG. 5, since the ratio does not exceed the threshold value, the highest signal-change value is assigned at the temperature for the first signal-change value and two temperatures. two temperatures being apart from the temperature for the first signal-change value in the same interval are selected. In this case, interpolated temperatures between T1 and T2 and between T4 and T5 were selected.

For example, if T2, T3, T4 and T5 are 70° C., 72° C., 74° C. and 76° C., respectively, then the interpolated temperature between T2 and T3 is 71° C., the interpolated temperature between T3 and T4 is 73° C., and the interpolated temperature between T4 and T5 is 75° C. Therefore, the reference temperatures are selected as 71° C. and 75° C.

The signal change value between detected temperatures may be calculated in various ways.

In an embodiment, the signal change value of signal values between two immediately adjacent detection temperatures may be calculated by a subtraction, a ratio, or a rate of change.

Another method of selecting reference temperatures using signal values at a plurality of detection temperatures for a corresponding target nucleic acid sequence comprise utilizing the signal values at the plurality of detection temperatures to determine a real reaction $T_m$ and selecting reference temperatures for the target nucleic acid sequence to include the measured $T_m$.

The term "real reaction $T_m$" refers to a $T_m$ value which is actually exhibited by a duplex formed during the sample analysis for a corresponding target nucleic acid sequence. The real reaction $T_m$ may depend upon the reaction environment (e.g., temperature, salt concentration, divalent cation concentration, oligosaccharide concentration, pH, etc.).

The term "expected $T_m$" refers to a $T_m$ value which is expected to be exhibited by a duplex formed during the sample analysis for a corresponding target nucleic acid sequence. The expected $T_m$ may be obtained through an experiment using a standard for the target nucleic acid sequence. Alternatively, the expected $T_m$ may be obtained by using a $T_m$ analysis program known in the art.

In an embodiment, the present method further comprises calculating a real reaction $T_m$ value of the duplex for the corresponding target nucleic acid sequence with the signal values at the at three detection temperatures.

In an embodiment, the two reference temperatures are selected such that a real reaction $T_m$ value of the duplex for each corresponding target nucleic acid sequence is included between the two reference temperatures.

In one embodiment, a melt analysis can be carried out at at least cycles to obtain a real reaction $T_m$ for the target nucleic acid sequence. The melt analysis can be performed at the end cycle or at an intermediate cycle. In one embodiment, the melt analysis is performed by increasing or decreasing the temperature at an interval of 0.5° C. or less within a certain temperature range to obtain a data set of temperature/signal value.

In the case of selecting suitable reference temperatures from the real reaction results, the temperature range in which the amount of a duplex is expected to be changed based on an expected $T_m$ value may differ from the temperature range in which the amount of a duplex is actually changed. As used herein, the term "the reference temperatures fall within a temperature range in which the amount of a duplex is changed" is intended to encompass that the reference temperatures fall within the temperature range in which the amount of a duplex is expected to be changed based on an expected $T_m$, as well as that the reference temperatures fall within the temperature range in which the amount of a duplex is actually changed.

In one embodiment, the reference temperatures for a corresponding target nucleic acid sequence may be selected for each reaction vessel. In one embodiment, when the same target nucleic acid sequence is detected in different reaction vessels (particularly in the case of using a label having the same signal property in the reaction vessels), reference temperatures for the corresponding target nucleic acid sequence are selected for each of the reaction vessels, and representative reference temperatures for the corresponding target nucleic acid sequence are determined from them and applied to all reaction vessels. In one embodiment, when the same target nucleic acid sequence is detected in different reaction vessels, information for selecting reference temperatures for the corresponding target nucleic acid sequence is collected from each of the reaction vessels, and representative reference temperatures are determined from the information and applied to all reaction vessels. The reference temperatures are selected from temperatures at which a signal change value indicating the presence of the target nucleic acid sequence can be provided.

In one embodiment, the two reference temperatures for each target nucleic acid sequence are selected from a temperature range in which the amount of a duplex for the corresponding target nucleic acid sequence is changed. In another embodiment, one of the two reference temperatures for each target nucleic acid sequence is selected from a temperature range in which the amount of a duplex for the corresponding target nucleic acid sequence is changed, and the other is selected from a temperature range in which the amount of a duplex for the corresponding target nucleic acid sequence remains unchanged. In one embodiment, one of the two detection temperatures for each target nucleic acid sequence is selected from a temperature range in which the duplex is in a hybridized state and the other is selected from a temperature range in which the duplex is in a dissociated state.

In one embodiment of the invention, the two reference temperatures for each target nucleic acid sequence are selected from temperatures which fall within a temperature range in which the amount of a duplex for the corresponding target nucleic acid sequence is changed but do not fall within a temperature range in which the amount of duplexes for other target nucleic acid sequences remains substantially unchanged.

In one embodiment, at least two of the detection temperatures within the detection temperature range for each target nucleic acid sequence comprise those at which the signal change value thereof can indicate the presence of the target nucleic acid sequence, and the reference temperatures are selected from the at least two temperatures.

In one embodiment, the two reference temperatures differ from each other by no more than no more than 5° C., no more than 4° C., no more than 3° C., no more than 2° C. or no more than 1° C. In other word, the difference between the first and second reference temperature is no more than no more than 5° C., no more than 4° C., no more than 3° C., no more than 2° C. or no more than 1° C.

In one embodiment, the two reference temperatures have a temperature difference of no less than 0.1° C., no less than 0.5° C., no less than 1° C., no less than 1.5° C. or no less than 2° C.

In one embodiment, the two reference temperatures differ from each other by 1° C.-5° C., 1° C.-4° C., 1° C.-3° C., 2° C.-5° C., 2° C.-4° C. or 2° C.-3° C., particularly, by 1° C.-4° C. or 2° C.-4° C.

The present inventors have found that when a target nucleic acid sequence is detected by using a duplex containing a labeled oligonucleotide, in particular, by using a duplex formed in a dependent manner on a mediation oligonucleotide-involving cleavage, the target nucleic acid sequence can be detected even using two reference temperatures having a difference of 5° C. or less. Further, it was found that the hybridization can be controlled in a sensitive manner to the temperature change by using a duplex of a shorter length than a conventional amplicon of a target nucleic acid sequence and thus a detectable signal, i.e., a significant signal change value, can be provided even at a small temperature difference.

The reference temperatures constitute a temperature range in which the change in the signal generated from a duplex for another target nucleic acid sequence is very small compared with that for a corresponding target nucleic acid sequence. For example, the change in the signal generated from a duplex for another target nucleic acid sequence may be no more than 10%, 9%, 8%, 7%, 6%, 5%, 4%, 3%, 2%, or 1% compared with the change in the signal generated from a duplex for a corresponding target nucleic acid sequence.

Obtaining a Signal-Change Value

A signal-change value for the corresponding target nucleic acid sequence is obtained from the signal values between the two reference temperatures.

As used herein, the term "signal values between the two reference temperatures" is intended to encompass not only signal values at two reference temperatures, but also signal values at all or some of temperatures therebetween.

For example, if the detection temperatures for the corresponding target nucleic acid sequence are 60° C., 61.5° C., 63° C., 64.5° C., and 65° C., and 61.5° C. and 64.5° C. are selected as the two reference temperatures, "signal values between the two temperatures" may indicate signal values at 61.5° C. and 64.5° C.; signal values at 61.5° C., 63° C. and 64.5° C.; or signal values at 61.5° C. and 63° C.

In one embodiment, the signal-change value is obtained by using two signal values at the two reference temperatures.

The term "signal values between the two reference temperatures" may be replaced with "signal values at any temperatures between the two reference temperatures".

In one embodiment of the present invention, "signal values between the two reference temperatures" also encompass, if present, one or more signal values at one or more interpolated temperatures.

The term "obtaining a signal-change value of signal values between the two reference temperatures" refers to obtaining a signal-change value of all or some of signal values between two reference temperatures in a defined manner.

The calculation of the signal-change value from the signal values can be defined in a variety manner. In one example, the signal-change value may be obtained by a subtraction, a ratio, or a rate of change for two signal values. In another example, the signal-change value may be obtained by a subtraction, a ratio, or a rate of change for three or more signal values between reference temperatures. Specifically, the subtraction for three or more signal values may be accomplished by obtaining subtracted values between adjacent signal values and determining a highest value, a lowest value, or an average from the subtracted values. The ratio for three or more signal values may be accomplished by obtaining ratio values between adjacent signal values and determining a highest value, a lowest value, or an average from the ratio values. The rate of change for three or more signal values may be accomplished by determining an average slope of the three or more signal values. If there are three or more signal values, a number of methods can be used to calculate a subtraction, a ratio, or a rate of change of the three or more signal values.

In one embodiment, obtaining the signal-change value from the signal values at the two reference temperatures is by the difference of the signal values.

In another embodiment of the present invention, obtaining the signal-change value from the signal value between the two reference temperatures is by the difference of the signal values relative to the temperature change value. The temperature change value may be the difference of the two reference temperatures. For example, if the reference temperatures are 61° C. and 63° C., the temperature change value is 2° C. When 630 RFU (relative fluorescent units) is detected at 61° C. and 600 RFU is detected at 63° C., the difference of the signal values is 30 RFU. In this case, the signal-change value equals to 30 RFU/2° C., i.e., 15 RFU 1° C.

In one embodiment, where there are three or more signal values between the reference temperatures, a straight line fitted to three or more signal values may be plotted, and then the slope of the straight line may be taken as the signal-change value.

Once two reference temperatures for each target nucleic acid sequence are determined, a signal-change value for the corresponding target nucleic acid sequence is obtained using the signal values at the two reference temperatures and the signal value at the interpolated cycle, thereby obtaining a data set of cycle/signal-change value.

The data set of cycle/signal-change value may be obtained for each target nucleic acid sequence. The data set of cycle/signal-change value includes a cycle at which a signal value is measured and a signal-change value calculated from the signal values between the reference temperatures at the cycle.

The data set of cycle/signal-change value comprises data points.

The term "data point" as used herein means a coordinate value comprising a cycle and a signal-change value at the cycle. The term "data" means all information that constitutes a dataset. For example, each of the cycles and the signal-change values is a data.

Data points can be represented as coordinate values in a two-dimensional rectangular coordinate system. In the coordinate values, the X-axis represents the cycle number, and the Y-axis represents the signal-change value calculated at the cycle number.

The term "dataset" as used herein refers to a set of data points.

The dataset may be plotted, giving an amplification curve.

In one embodiment, a data set for a target nucleic acid sequence, which is obtained by a signal-generating reaction, is a data set indicative of the presence or absence of the target nucleic acid sequence.

Step: Determining the Presence or Absence of the Plurality of Target Nucleic Acid Sequences (150)

The presence or absence of each of the plurality of target nucleic acid sequences in the sample is determined by the data set of cycle/signal-change value.

Since the data set of cycle/signal-change value is generated for each of the plurality of target nucleic acid sequences, the data set of cycle/signal-change value can be used to determine the presence or absence of the corresponding target nucleic acid sequence.

In one embodiment, the presence or absence of the target nucleic acid sequence is determined by whether the data set of cycle/signal-change value exceeds a threshold value. If the data set of cycle/signal-change value exceeds a threshold value, it is determined that a target nucleic acid sequence corresponding to the data set of cycle/signal-change value is present in a sample. The threshold value may be set to RFU 80, 90, 100, 110, 120, 130, or more.

In one embodiment, the presence or absence of a target nucleic acid sequence is performed by using a nonlinear function fitted to the data set of cycle/signal-change value. In one example, the non-linear function may be a sigmoid function.

For example, the sigmoid function may be represented by Equation 1.

$$f(x) = a_1 + \frac{a_2 - a_1}{1 + 10^{a_4(a_3 - x)}} \quad \langle \text{Equation 1} \rangle$$

wherein f(x) is a sigmoid function; $a_1$ is the lowest value of the data set of cycle/signal-change value; $a_2$, $a_3$ and $a_4$ are determined by fitting with the data set of cycle/signal-change value.

In one embodiment of the invention, the presence or absence of a target nucleic acid sequence is determined by comparing the maximum slope, the maximum value, or the fitting accuracy of the nonlinear function fitted to the data set of cycle/signal-change value with the respective threshold value. When all of the maximum slope, the maximum value, and the fitting accuracy of the nonlinear function exceed the respective threshold value, it is determined that the target nucleic acid sequence is present. Alternatively, if either of the maximum slope, the maximum value, or the fitting accuracy of the nonlinear function exceeds the respective threshold value, it is determined that the target nucleic acid sequence is present.

For example, the threshold value for the maximum slope may be set to 15, 20, 25, 30, 35, 40, and the like. The threshold value for the maximum value may be set to RFU 80, 90, 100, 110, 120, 130, 140, 150, or less.

The fitting accuracy encompasses a value indicating (a) how closely the nonlinear function can predict the data set of cycle/signal-change value, i.e., the goodness of fit; and (b) how useful the explanatory variables are in predicting response variables.

The fitting accuracy may indicate the degree of match between the non-linear function and the data set of cycle/signal-change value. Further, the fitting accuracy represents the difference between the non-linear function and the data set of cycle/signal-change value. The fitting accuracy increases as the match between the nonlinear function and the data set of cycle/signal change increases. For example, the fitting accuracy may be an X-square value (chi-square value) or an R-square value.

In one embodiment of the invention, a data set of cycle/signal value consisting of signal values at each of all or some of the cycles is restored from the data set of cycle/signal-change value and is used to determine the presence or absence of the target nucleic acid sequence. The data set of cycle/signal value is one which is generated by detecting signal values at each cycle. Typically, signal values are detected at a temperature at which the amount of a duplex for the target nucleic acid sequence is at its maximum to generate a data set of cycle/signal value. The temperature at which the amount of the duplex is at its maximum may be one at which the intensity of the signal by the duplex is at its maximum. According to the present invention, a data set of cycle/signal value may be derived from a data set of cycle/signal-change value.

Restoration of a Data Set of Cycle/Signal Value

In an embodiment, signal values can be restored from the data set of cycle/signal-change value for each corresponding target nucleic acid sequence to obtain a restored data set of cycle/signal value, and the determination of the presence or absence of the plurality of target nucleic acid sequences in the sample is performed by using the restored data set of cycle/signal value.

In an embodiment, the restored signal values are signal values at temperature at which a duplex for each corresponding target nucleic acid sequence generates a highest signal value.

In an embodiment, the cycle/signal value data set is restored from the cycle/signal-change value using the following equation 2.

$$\text{CYCLE} - \text{SIGNAL DATA SET}(FDT, \text{Cycle}) = \left[ \frac{SV(FDT, FC) - BSV}{\frac{\partial SV(SCT, FC)}{\partial T}} \right] \times \frac{\partial SV(SCT, \text{Cycle})}{\partial T} + BSV \quad \text{⟨Equation 2⟩}$$

wherein FDT is a certain temperature, which may be designated by the user; FC denotes an end cycle; SCT is a temperature at which a signal-change value is detected; the BSV is a background signal value; SV denotes a signal value; and ∂SV/∂T denotes a signal-change value.

The FDT may be a temperature at which the signal from the duplex is a maximum. Alternatively, the FDT may be a certain temperature within the detection temperature range or outside the detection temperature range. For example, where the Tm value of a duplex generated by a signal-generating composition is 65° C., SCT may be set to 65° C. and FDT may be set to 60° C.

Equation 2 can be derived as shown in the following Equation 3 to Equation 4 by the method of separation of variables.

Figure 6:
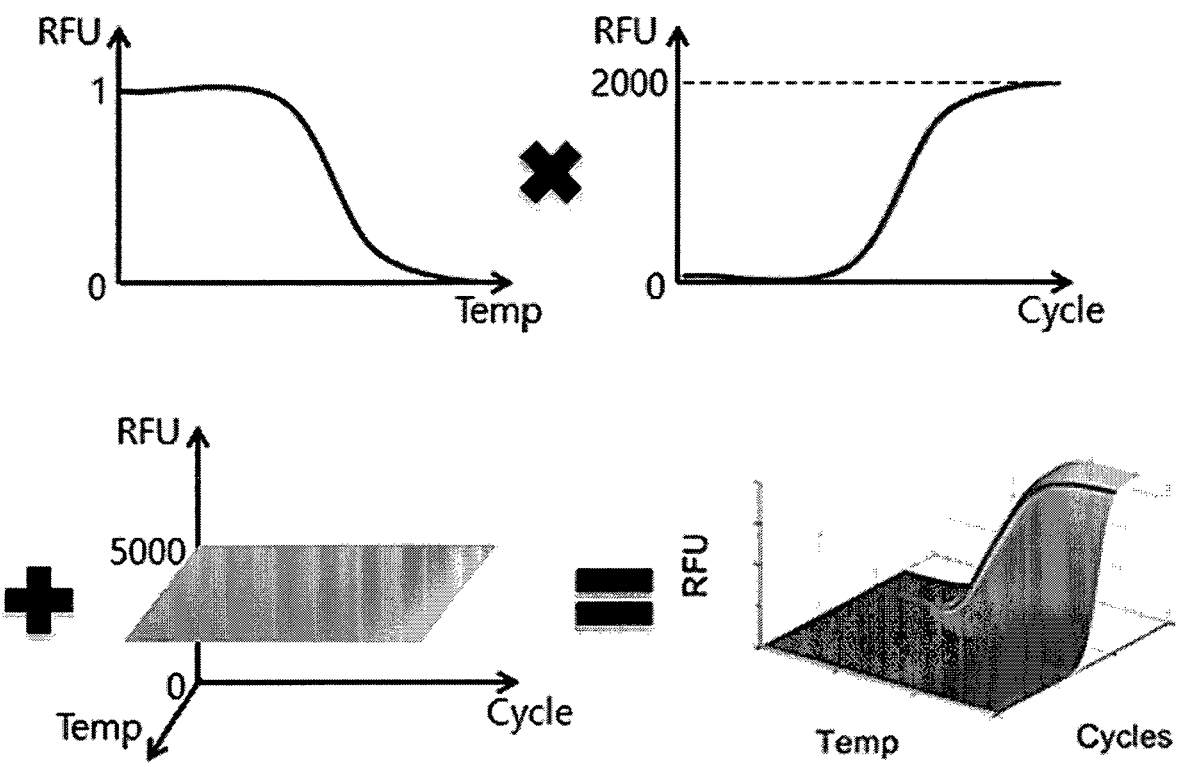
FIG. 6 illustrates a method of a separation of variables.

In the method of separation of variables, RFU(T, C) may be expressed with f(T), g(C) and "a". RFU(T, C) is a function representing signal values detected by the detection device. T represents the temperature, and C represents the cycle. That is, RFU(T, C) represents signal values as a function of temperature "T" and cycle "C". f(T) represents signal values as a function of temperature "T", and g(C) represents signal values as a function of cycle "C". "a" represents a background signal (see FIG. 6).

Hereinafter, it is illustrated how Equation 2 used to restore the cycle/signal value data set at 60° C. from the cycle/signal-change value data set at 65° C. can be derived.

Equation 3 represents the cycle/signal value data set obtained at 60° C. and cycle "C" according to the method of separation of variables. "a" represents the background signal value as measured at 45 cycle and at 85° C.

$$RFU(60, C) = f(60)g(C) + \alpha \quad \text{<Equation 3>}$$

In Equation 3, RFU(60,C) is represented by the multiplication of the function f(T) and the function g(C).

Equation 4 represents the cycle/signal value data set at 65° C. and at cycle "C" according to the method of separation of variables.

The function g(c) is independent on a temperature, as it is a function of only cycle "C". Differentiating both sides with temperature "T" gives the function g(c) represented by the signal change values such as RFU(65,C) and f(65).

$$RFU(65, C) = f(65)g(C) + \alpha \quad \text{⟨Equation 4⟩}$$

$$\Rightarrow \frac{\partial RFU}{\partial T}(65, C) = \frac{df}{dT}(65)g(C)$$

-continued $$\Rightarrow g(C) = \frac{\partial RFU}{\partial T}(65, C) \bigg/ \frac{df}{dT}(65)$$

Equation 5 represents the equation obtained by substituting g(C) of Equation 4 for g(C) of Equation 3.

$$RFU(60, C) = \frac{f(60)}{\frac{df}{dT}(65)} \frac{\partial RFU}{\partial T}(65, C) + \alpha \quad \text{⟨Equation 5⟩}$$

Equation 6 represents the signal value detected at $45^{th}$ cycle and at 60° C. The Equation 6 is rearranged for f(60). In this example, $45^{th}$ cycle is the end cycle.

$$RFU(60, 45) = f(60)g(45) + \alpha \quad \text{⟨Equation 6⟩}$$

$$\Rightarrow f(60) = \frac{RFU(60, 45) - \alpha}{g(45)}$$

Equation 7 represents an equation obtained by differentiation of the equation 6 with temperature "T". The equation 7 is rearranged for the derivative of f(65) with respect to temperature "T".

$$\frac{\partial RFU}{\partial T}(65, 45) = \frac{df}{dT}(65)g(45) \quad \text{⟨Equation 7⟩}$$

$$\Rightarrow \frac{df}{dT}(65) = \frac{\frac{\partial RFU}{\partial T}(65, 45)}{g(45)}$$

Equation 8 represents a re-expressed Equation 5 by substituting some terms with the corresponding terms in Equation 6 and Equation 7.

$$RFU(60, C) = \frac{RFU(60, 45) - \alpha}{\frac{\partial RFU}{\partial T}(65, 45)} \frac{\partial RFU}{\partial T}(65, C) + \alpha \quad \text{⟨Equation 8⟩}$$

$$\approx \frac{RFU(60, 45) - RFU(85, 45)}{\frac{\partial RFU}{\partial T}(65, 45)} \frac{\partial RFU}{\partial T}(65, C) + RFU(85, 45)$$

The values of the equation 8 may be obtained by detecting the signal value and the signal-change value at 45 cycle, except for the signal change value at 65° C. in each cycle. Therefore, equation 8 may be simplified as Equation 9.

$$RFU(60, C) = A \frac{\partial RFU}{\partial T}(65, C) + B \quad \text{⟨Equation 9⟩}$$

Since A and B may be obtained by detecting the signal value and/or the change value at $45^{th}$ cycle, these are expressed by constants.

Consequently, the signal values at 60° C. at each cycle may be generated by a formula comprising (i) the signal value at 60° C. and at $45^{th}$ cycle; (ii) the signal value at 85° C. and at $45^{th}$ cycle; (iii) the signal-change values at 65° C. and at each cycle; and (iv) the signal value at 65° C. and at $45^{th}$ cycle.

Generally, since the prior art detects the signal value at 60° C. to obtain a data set, the resultant data set may comprise a signal generated by a nucleic acid sequence other than the target nucleic acid sequence, leading to false positives.

On the other hand, since the present invention uses a signal-change values at 65° C. to obtain a cycle/signal value data set, the resultant data set does not comprise a signal generated by the nucleic acid sequence other than the target nucleic acid sequence, unless the signal generated by the nucleic acid sequence other than the target nucleic acid sequence is changed at 65° C. Therefore, the present invention has an advantage of remarkably reducing the false positives compared with the prior art.

When Equation 9 is applied to two target nucleic acid sequences, the signal value for the first target nucleic acid sequence may be represented as shown in Equation 10, and the signal value for the second target nucleic acid sequence may be represented as shown in Equation 11.

$$RFU1(60, \text{Cycles}) = \left[\frac{RFU1(60, 45) - \alpha}{\frac{\partial RFU1(65, 45)}{\partial T}}\right] \cdot \frac{\partial RFU1(65, C)}{\partial T} + \alpha \quad \langle \text{Equation 10} \rangle$$

$$= \left[\frac{RFU(60, 45) - RFU(72, 45) - \alpha}{\frac{\partial RFU(65, 45)}{\partial T}}\right] \cdot \frac{\partial RFU(65, C)}{\partial T} + \alpha$$

$$RFU2(72, \text{Cycles}) = \left[\frac{RFU2(72, 45) - \alpha}{\frac{\partial RFU2(77, 45)}{\partial T}}\right] \cdot \frac{\partial RFU2(77, C)}{\partial T} + \quad \langle \text{Equation 11} \rangle$$

$$\alpha = \left[\frac{RFU(72, 45) - \alpha}{\frac{\partial RFU(77, 45)}{\partial T}}\right] \cdot \frac{\partial RFU(77, C)}{\partial T} + \alpha$$

In Equations 10 and 11, RFU1 represents the signal value for the first target nucleic acid sequence and RFU2 represents the signal value for the second target nucleic acid sequence. RFU1 (60, Cycles) represents a cycle/signal value data set consisting of cycles and signal values at the cycles, detected at 60° C. in the presence of the first target nucleic acid sequence alone. RFU2 (72, Cycles) represents a cycle/signal value data set consisting of cycles and signal values at the cycles, detected at 72° C. in the presence of the second target nucleic acid sequence alone.

In addition, ∂RFU1(65, c)/∂T represents the signal-change value at 65° C. and at cycles in the presence of the first target nucleic acid sequence alone. ∂RFU(65, c)/∂T represents the signal-change value at 65° C. and at cycles in the presence of both of the first target nucleic acid sequence and the second target nucleic acid sequence in a single vessel. Because the signal value for the first target nucleic acid sequence is changed but the signal value for the second target nucleic acid sequence remains substantially unchanged at 65° C., ∂RFU1(65, c)/∂T may be assumed to be equal to ∂RFU(65, c)/∂T.

Further, ∂RFU2(77, c)/∂T represents the signal-change value at 77° C. and at cycles in the presence of the second target nucleic acid sequence alone. ∂RFU (77, C)∂T represents the signal-change value at 77° C. and at cycles in the presence of both of the first target nucleic acid sequence and the second target nucleic acid sequence in a single vessel. Because the signal value for the second target nucleic acid sequence is changed but the signal value for the first target nucleic acid sequence remains substantially unchanged at 77° C., ∂RFU2(77, c)/∂T may be assumed to be equal to ∂RFU(77, C)/∂T.

Consequently, the cycle/signal value data set for the first target nucleic acid sequence and the cycle/signal value data set for the second target nucleic acid sequence may be simplified as in equation 12.

$$RFU1(60, \text{Cycles}) = C \cdot \frac{\partial RFU(65, C)}{\partial T} + D \quad \langle \text{Equation 12} \rangle$$

$$RFU2(72, \text{Cycles}) = E \cdot \frac{\partial RFU(77, C)}{\partial T} + D$$

In Equation 12, since C, D, and E may be obtained from the signal values and/or signal-change values detected at the end cycle, these are expressed as constants.

In conclusion, the present invention may restore cycle/signal value data set from signal change values for a plurality of target nucleic acid sequences by designing oligonucleotides such that the temperature ranges for a plurality of target nucleic acid sequences do not overlap with each other, wherein each of the temperature range is a range in which the signal for the corresponding target nucleic acid sequence is changed.

As illustrated above, the present invention provides a method for restoring a cycle/signal value data set at a first temperature from a cycle/signal change value data set at a second temperature, comprising the steps of:
 (a) obtaining a cycle/signal change value data set at a second temperature;
 (b) obtaining the following values:
  (i) a signal value at an end cycle and at a first temperature;
  (ii) a background signal value; and
  (iii) a signal value at an end cycle and at the second temperature; and
 (c) applying the values obtained in step (b) to an equation capable of transforming the cycle/signal change value data set at the second temperature into the cycle/signal value data set at the first temperature, thereby obtaining the cycle/signal value data set at the first temperature.

The equation in step (c) may comprise a coefficient, ([a signal value at an end cycle and at a first temperature minus a background signal value] divided by [a signal value at an end cycle and at the second temperature]).

Examples of the equation in step (c) includes, but not limited to, Equation 2.

Combination of a Different Signal-Generating Method for Target Detection

In an embodiment, the signal-generating compositions comprise a composition which comprises a labeled oligonucleotide for generating a detectable signal by a cleavage reaction dependent on the presence of one of the plurality of target nucleic acid sequences, the labeled oligonucleotide is cleaved by a nuclease in the duplex reaction, and obtaining the signal values is performed at temperature at which all duplexes for the other target nucleic acid sequences of the plurality of target nucleic acid sequences are hybridized or dissociated to generate no signals; wherein the label in the labeled oligonucleotide for generating a detectable signal by a cleavage reaction has the same signal property to the labels in the duplexes.

The present method described above determines the presence or absence of target nucleic acid sequences of interest by forming duplexes for the target nucleic acid sequences and obtaining the signal-change values between two different temperatures from the duplexes.

Duplexes for the different target nucleic acid sequences include labels having the same signal property. Therefore, signals detected by a detector cannot be differentiated into which duplexes generate signal. However, the duplexes can provide signal-change values indicating the presence of the corresponding target nucleic acid sequences as the duplexes have different Tm values from each other.

In the present method, one of a plurality of target nucleic acid sequences can be detected by cleaving a labeled oligonucleotide in a dependent manner on the presence of that target nucleic acid sequence and measuring the signal generated by the cleavage at a temperature. Particularly, a label linked to the oligonucleotide to generate a signal by cleavage can have the same signal property to labels used for the duplexes.

In an embodiment, the cleavage of the detection oligonucleotide induces signal changes or releases a labeled fragment to be detected.

Where the signal is generated by cleavage of the labeled oligonucleotide, signal from a released label by the cleavage may be detected at any temperatures. Therefore, any temperatures may be selected so long as the signal generated by cleavage of a detection oligonucleotide may be detected.

In an embodiment, a signal generated by cleavage of a labeled oligonucleotide is detected at a temperature at which all duplexes for the other target nucleic acid sequences of the plurality of target nucleic acid sequences are hybridized or dissociated to generate no signals.

For example, where duplexes labeled such that the duplexes dissociated to be single-stranded do not generate signals, a signal generated by cleavage of the labeled oligonucleotide is detected at a temperature at which all duplexed expected to be formed is sufficiently dissociated.

For example, where duplexes labeled such that the duplexes hybridized do not generate signals, a signal generated by cleavage of the labeled oligonucleotide is detected at a temperature at which all duplexed expected to be formed is sufficiently hybridized.

Intensity of signal from a released label generated by cleavage of the labeled oligonucleotide may be changed depending on a temperature. Such phenomenon may cause false positive results in determining the presence of the target nucleic acid sequences by a formation of duplex. The present method enables to apply, 5° C. or less, 4° C. or less, 3° C. or less or 2° C. or less interval between two reference temperatures selected for calculating signal-change value, which reduces the possibility of such false results.

In an embodiment, at least two target nucleic acid sequences are detected by generating signals by formation of duplexes and one target nucleic acid sequence is detected by generation a signal by cleavage of a labeled oligonucleotide. According to an embodiment, 1, 2, 3, 4, 5, 6, 7, 8, 9, or 10 of target nucleic acid sequences is detected by generating signals by formation of duplexes and one target nucleic acid sequence is detected by generation a signal by cleavage of a labeled oligonucleotide.

In an embodiment, the signal-generating compositions comprise a composition which comprises a labeled oligonucleotide for generating a detectable signal by a cleavage reaction dependent on the presence of one of the plurality of target nucleic acid sequences and the labeled oligonucleotide is cleaved by a nuclease in the reaction.

Particularly, a signal-generating composition may be used, which generates a signal by hybridization of the labeled oligonucleotide with a target nucleic acid sequence and then cleavage of the labeled oligonucleotide.

The signal by hybridization of the detection oligonucleotide with a target nucleic acid sequence and then cleavage of the detection oligonucleotide may be generated by various methods, including TaqMan probe method (U.S. Pat. Nos. 5,210,015 and 5,538,848).

Where the signal is generated by TaqMan probe method, the signal-generating composition includes a primer set for amplification of a target nucleic acid sequence, TaqMan probe having a suitable label (e.g., interactive dual label) and nucleic acid polymerase having 5'-nuclease activity. The TaqMan probe hybridized with a target nucleic acid sequence is cleaved during target amplification and generates signal indicating the presence of the target nucleic acid sequence.

The particular example generating signal by TaqMan probe method comprises the step of: (a) hybridizing the primer set and TaqMan probe having a suitable label (e.g., interactive dual label) with the target nucleic acid sequence; (b) amplifying the target nucleic acid sequence by using the resultant of the step (a) and nucleic acid polymerase having 5'-nuclease activity, wherein the TaqMan probe is cleaved to release the label; and (c) detecting a signal generation from the released label.

Particularly, a signal-generating composition may be used, which generates a signal by cleavage of the detection oligonucleotide in a dependent manner on a mediation oligonucleotide-involving cleavage.

In an embodiment, where a mediation oligonucleotide-involving cleavage releases a fragment, the fragment is specifically hybridized with a detection oligonucleotide and the fragment induces the cleavage of the detection oligonucleotide.

In an embodiment, where a mediation oligonucleotide-involving cleavage releases a fragment, the fragment is extended to cleave a labeled oligonucleotide comprising a hybridizing nucleotide sequence complementary to the capture oligonucleotide.

The signal by cleavage of the detection oligonucleotide in a dependent manner on a mediation oligonucleotide-involving cleavage may be generated by various methods, including Invader assay (U.S. Pat. No. 5,691,142), PCEC (PTO Cleavage and Extension-Dependent Cleavage) method (WO 2012/134195), PCE-SC (PTO Cleavage and Extension-dependent Signaling Oligonucleotide Cleavage) (WO 2013/157821), and a method described in U.S. Pat. No. 7,309,573. In particular, the method described in U.S. Pat. No. 7,309,573 may be considered as one of PTOCE-based methods using signal generation by cleavage, and in the method, the formation of the extended strand may be detected by detecting cleavage of an oligonucleotide specifically hybridized with the CTO by the formation of the extended strand. Invader assay forms a fragment by cleavage of a mediation oligonucleotide and induces successive cleavage reactions with no extension of the fragment.

In an embodiment, the combination of (i) for a target nucleic acid sequence, a signal-generating composition to generate a signal in a dependent manner on cleavage of a labeled oligonucleotide (e.g., TaqMan method) and (ii) for another target nucleic acid sequence, a signal-generating composition to provide a signal by a duplex formed in a dependent manner on a mediation oligonucleotide-involving cleavage, particularly cleavage of a mediation oligonucleotide, can induce the unexpected results.

The method using cleavage of the detection oligonucleotide generally uses enzyme having 5' nuclease activity (particularly, Taq polymerase) for cleavage of the detection oligonucleotide. In the conventional methods to generate signal by direct hybridization of detection probes (e.g., Molecular beacon method, hybridization probe method or Hybeacon method), the detection probes are very likely to be cleaved by the enzyme having 5' nuclease activity (particularly, Taq polymerase). The cleavage of the detection probes may cause decease in sensitivity due to consumption of the detection probes (e.g., hybridization probe method) or false positive signal in methods with cleavage-dependent signaling (e.g., Molecular beacon method). Although the labeled primer methods (e.g., Sunrise method or Scorpion method) do not suffer from the cleavage as the probe methods, they have shortcomings in which $T_m$ value of amplicon per se has to be controlled to adjust detection temperatures. In contrast, because the methods including the step of cleavage of a mediation oligonucleotide employ cleavage of the mediation oligonucleotide specifically hybridized with the target nucleic acid sequence, they are not affected by enzyme having 5' nuclease activity (particularly, Taq polymerase). In addition, the methods including the step of cleavage of a mediation oligonucleotide, particularly the PTOCE-based methods, can readily adjust $T_m$ value of duplex formed to ensure convenient selection of detection temperatures.

II. Detection of a Target Nucleic Acid Sequence in a Sample Using a Signal-Change Value In another aspect of this invention, there is provided a method for detecting a target nucleic acid sequences in a sample, comprising:

contacting in a reaction vessel the sample to a signal-generating composition for detecting the target nucleic acid sequence; wherein the signal-generating composition forms a duplex for the target nucleic acid sequence and the duplex provides a signal indicating the presence or absence of the target nucleic acid sequence;

performing a reaction for at least two cycles for (i) the formation of the duplex and (ii) a hybridization and/or dissociation of the formed duplex;

obtaining at all or partial cycles of the reaction signal values at at least two detection temperatures in a detection temperature range assigned to the target nucleic acid sequence; wherein the detection temperature range comprises a temperature range in which the amount of the duplex is changed;

obtaining a signal-change value of signal values between two reference temperatures selected from the at least two detection temperatures in the detection temperature range such that a data set of cycle/signal-change value for the target nucleic acid sequence is obtained; and determining the presence or absence of the target nucleic acid sequence in the sample by the data set of cycle/signal-change value for the target nucleic acid sequence.

Since the present invention follows in principle the first aspect of this invention described above, the common descriptions between them are omitted in order to avoid undue redundancy leading to the complexity of this specification.

In one embodiment, the signal-generating composition comprise oligonucleotides for formation of the duplexes which provides the signal indicating the presence of the corresponding target nucleic acid sequence, the oligonucleotides comprise labeled oligonucleotides, the duplexes comprise a labeled oligonucleotide and the hybridization and/or dissociation of the formed duplex provides a detectable signal.

In one embodiment, the duplex is (i) a duplex formed by hybridization between the target nucleic acid sequence and a labeled oligonucleotide, (ii) a duplex formed by hybridization between an oligonucleotide comprising a hybridizing sequence complementary to the target nucleic acid sequence and a labeled oligonucleotide complementary to at least a portion of the hybridizing sequence or (iii) a duplex formed in a dependent manner on a mediation oligonucleotide-involving cleavage wherein the mediation oligonucleotide is the hybridized with the target nucleic acid sequence.

In one embodiment, the duplex formed in a dependent manner on the mediation oligonucleotide-involving cleavage is a duplex formed in a dependent manner on formation of an extended strand which is formed by extension of a fragment released by the mediation oligonucleotide-involving cleavage.

In one embodiment, the duplex formed in a dependent manner on a mediation oligonucleotide-involving cleavage is a duplex formed by hybridization of a fragment released by the mediation oligonucleotide-involving cleavage with a counterpart oligonucleotide.

In one embodiment, when temperatures and signal values thereof are interpolated from the at least two detection temperatures, the at least two detection temperatures comprise the interpolated detection temperatures.

In one embodiment, the at least two detection temperatures are 2-10 in number.

In one embodiment, the two reference temperatures differ from each other by no more than 5° C., no more than 4° C., no more than 3° C., no more than 2° C. no more than 1° C.

In one embodiment, the at least two detection temperatures is no less than 3 in number; the method further comprises analyzing the signal values at the at least three detection temperatures to select the at least two reference temperatures.

In one embodiment, the sample comprises an additional target nucleic acid sequence and the signal-generating composition further comprises a composition which comprises a labeled oligonucleotide for generating a detectable signal by a cleavage reaction dependent on the presence of the additional target nucleic acid sequences, the labeled oligonucleotide is cleaved by a nuclease in the duplex reaction, and obtaining the signal values is performed at temperature at which the duplex for the other target nucleic acid sequence is hybridized or dissociated to generate no signals; wherein the label in the labeled oligonucleotide for generating a detectable signal by a cleavage reaction has the same signal property to the labels in the duplexes.

III. Storage Medium and Device for Detection of Target Nucleic Acid Sequences by Signal-Change Value at the Two Reference Temperatures Since the storage medium, the device and the computer program of the prevent invention described herebelow are intended to perform the present methods in a computer, the common descriptions between them are omitted in order to avoid undue redundancy leading to the complexity of this specification.

In another aspect of this invention, there is provided a computer readable storage medium containing instructions to configure a processor to perform a method for detecting a plurality of target nucleic acid sequences in a sample, the method comprising:

receiving signal values; wherein the signal values are obtained by (i) contacting in a single reaction vessel a sample to signal-generating compositions for detecting a plurality of target nucleic acid sequences, wherein the signal-generating compositions form a plurality of duplexes for the plurality of target nucleic acid sequences, each of the plurality of duplexes provides a signal indicating the presence or absence of each corresponding target nucleic acid sequence and the plurality of duplexes have $T_m$ values different from each other; (ii) performing a reaction for at least two cycles for the formation of the plurality of duplexes and a hybridization and/or dissociation of the formed duplexes; and (iii) obtaining at all or partial cycles of the reaction signal values at at least two detection temperatures in each of a plurality of detection temperature ranges assigned to the plurality of target nucleic acid sequences, wherein each of the plurality of detection temperature ranges comprises a temperature range in which the amount of a duplex for each corresponding target nucleic acid sequence is changed;

generating a data set of cycle/signal-change value for each of the plurality of target nucleic acid sequences by obtaining a signal-change value of signal values between two reference temperatures selected from the at least two detection temperatures in each of the plurality of detection temperature ranges; and determining the presence or absence of the plurality of target nucleic acid sequences in the sample by the data set of cycle/signal-change value for each of the plurality of target nucleic acid sequences.

In still another aspect of this invention, there is provided a computer readable storage medium containing instructions to configure a processor to perform a method comprising:

receiving signal values; wherein the signal values are obtained by (i) contacting in a reaction vessel the sample to a signal-generating composition for detecting the target nucleic acid sequence; wherein the signal-generating composition forms a duplex for the target nucleic acid sequence and the duplex provides a signal indicating the presence or absence of the target nucleic acid sequence; (ii) performing a reaction for at least two cycles for (i) the formation of the duplex and (ii) a hybridization and/or dissociation of the formed duplex; and (iii) obtaining at all or partial cycles of the reaction signal values at at least two detection temperatures in a detection temperature range assigned to the target nucleic acid sequence; wherein the detection temperature range comprises a temperature range in which the amount of the duplex is changed;

generating a data set of cycle/signal-change value for the target nucleic acid sequence by obtaining a signal-change value of signal values between two reference temperatures selected from the at least two detection temperatures in the detection temperature range; and determining the presence or absence of the target nucleic acid sequence in the sample by the data set of cycle/signal-change value for the target nucleic acid sequence.

In still another aspect of this invention, there is provided a computer program stored on a computer readable storage medium to configure a processor to perform a method described above.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server. In one embodiment, the computer readable storage medium is a non-transitory the computer readable storage medium.

The data (e.g., intensity, amplification cycle number and detection temperature) associated with the signals may be received through several mechanisms. For example, the data may be acquired by a processor resident in a PCR data acquiring device. The data may be provided to the processor in real time as the data is being collected, or it may be stored in a memory unit or buffer and provided to the processor after the experiment has been completed. Similarly, the data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands In the present invention.

In still another aspect of this invention, there is provided a device for detecting a target nucleic acid sequence in a sample comprising (a) a computer processor and (b) the computer readable storage medium described above coupled to the computer processor.

In an embodiment, the device further comprises a reaction vessel to accommodate the sample and signal-generating composition, a temperature controlling means to control temperatures of the reaction vessel and/or a detector to detect signals at cycle numbers.

The processor may be prepared in such a manner that a single processor may do several performances. Alternatively, the processor unit may be prepared in such a manner that several processors do the several performances, respectively. In an embodiment, the processor may be embodied by installing software into conventional devices for detection of target nucleic acid sequences (e.g. real-time PCR device).

An analysis system includes an amplification device and an analysis device. The analysis system may determine the presence or absence of the target nucleic acid sequence in the sample and display a result to the user. The presence of the target nucleic acid sequence may be expressed as positive, and the absence as negative.

The amplification device is a device for performing a nucleic acid amplification reaction, an enzyme reaction, or a microbial growth. For example, when the amplification device performs the nucleic acid amplification reaction, the amplification device may repeatedly perform an operation of increasing or decreasing a temperature of samples. The amplification device may obtain a data set by measuring signals generated from the samples for each cycle.

The amplification device may be connected to the analysis device and a cable or wirelessly. The amplification device transmits the obtained data set to the analysis device via wired or wireless connection.

The analysis device obtains the data set from the amplification device. The analysis device analyzes the data set to determine whether a target nucleic acid sequence in the sample is present or absent. In other words, the analysis device determines the positive or negative for the sample.

The analysis device includes a display device. The display device may display a data set or display a floating data set as a graph. The display device may display a sigmoid function, a step function, or the like. In addition, the display device may display whether the target analyte is present or absent, and a detection result for each sample.

The analysis apparatus may read a data set included in a storage medium. The storage medium may store the data set, or may store programs and the like used in the analysis apparatus. The storage medium may be a CD, a USB, or the like.

The analysis apparatus may be a computer, a smartphone, a tablet or a wearable device. The analysis apparatus includes a processor, memory and display device.

The features and advantages of this invention will be summarized as follows:

(a) The present invention enables efficient detection of a plurality of target nucleic acid sequences in one detection channel, by obtaining a data set of cycle/signal-change value a signal-change value for a corresponding target nucleic acid sequence in a detection temperature range assigned to each of the plurality of target nucleic acid sequences.

(b) The present invention utilizes the signal generation from the duplexes containing a labeled oligonucleotide rather than the signal generation from the amplicons of the target nucleic acid sequences. These duplexes generally have a shorter length than the amplicons, and thus are more susceptible to hybridization or dissociation even at relatively small temperature changes. Further, the use of a duplex containing a labeled oligonucleotide allows signal-change values indicative of the presence of a target nucleic acid sequence to be provided even with reference temperatures spaced within 5° C.

(c) The present invention employs a plurality of duplexes containing a labeled oligonucleotide. These duplexes should be elaborately designed to have different Tm values. In an embodiment, the formation of duplexes in a dependent manner on a mediation oligonucleotide-involving cleavage is not affected by the target nucleic acid sequences, enabling the $T_m$ values of the duplexes to be freely adjusted. Thus, the formation of duplexes by the mediation oligonucleotide-involving cleavage can maximize the utility of the present invention.

(d) Conventional labeled oligonucleotides, particularly labeled probes, hybridizable with a target nucleic acid sequence may be cleaved during the reaction and compete with either strand of a double-stranded target nucleic acid sequence, resulting in a decrease in the signal-change value when a nucleic acid polymerase having 5' nuclease activity. In an embodiment, the duplex formation dependent on a mediation oligonucleotide-involving cleavage in accordance with the present invention can prevent such a decrease in the signal-change value.

(e) The invention employs two reference temperatures for each target nucleic acid sequence. Since the interval between the two reference temperatures can be set to be relatively narrow, e.g., within 5° C., the method of the present invention can eliminate the possibility that signal-change values for other target nucleic acid sequences may be included in the signal-change values at the two reference temperatures.

(f) The present invention enables the detection of a plurality of target nucleic acid sequences in a single reaction vessel using a single detection channel.

(g) The data set of cycle/signal-change value for each target nucleic acid sequence used in the present invention can provide a reduced noise signal, reduced inter-well or inter-instrument signal variation, or corrected baseline.

(h) The determination of the reference temperatures based on an expected Tm value of a duplex for the target nucleic acid sequence may be inappropriate due to the shift of the $T_m$ value in the actual reaction. The present invention allows selection of reference temperatures reflecting an actual reaction from a plurality of detection temperatures for each target nucleic acid sequence.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Detection of Target Nucleic Acid Sequence (Single Target)

Example 1 exemplified an embodiment of the present invention in which two detection temperatures were determined based on an expected $T_m$ value of a duplex for a target nucleic acid sequence and used as reference temperatures.

Preparation of Signal-Generating Composition

Four samples each was mixed with a signal-generating composition (i.e., oligonucleotide mixture and enzyme master mixture) contained in Allplex™ STI-GU kit (Seegene Inc., Cat. No. SD9802X) to detect *Chlamydia trachomatis* serovars L (CT).

The signal-generating composition contains a composition for forming a duplex providing a detectable signal for a target nucleic acid sequence by the PTOCE method. Where the target nucleic acid sequence is present in a sample, a mediation oligonucleotide (i.e., PTO) specifically hybridized with the target nucleic acid sequence is cleaved by a polymerase having 5'-nuclease activity and a cleavage fragment is hybridized with a capture oligonucleotide CTO) to be extended, thereby forming an extended duplex providing a detectable signal.

The expected $T_m$ of the extended duplex in the presence of CT is 64.5° C. The templating portion of the CTO has a dual label of Cal Red 610 and BHQ2. The four samples contain pDNA cloned with a CT sequence in the amounts of $10^6$ copies/reaction, $10^4$ copies/reaction, $10^3$ copies/reaction and $10^2$ copies/reaction, respectively. The reaction mixture for a real-time PCR amplification was prepared with Allplex™ STI-GU kit: Reaction mixture in the final volume of 20 µl containing 5 µl of 4×GU MOM, 5 µl of EM1, 5 µl of RNase-free Water and 5 µl of pDNA sample. MOM is an oligonucleotide mixture and EM1 is Taq polymerase.

Reaction and Obtaining Signal Values

Real-time PCR amplification reactions were carried out using the four reaction mixtures on CFX96 (Ver. 1.6, Bio-Rad, Inc.). The temperature and time profiles of the amplification reactions are summarized in Table 1.

TABLE 1

| Step | Temp. | Time (min:sec) | Cycle | Plate read |
|---|---|---|---|---|
| 1 | 50.0° C. | 4:00 | 1 | — |
| 2 | 95.0° C. | 15:00 | 1 | — |
| 3 | 95.0° C. | 00:30 | 5 | — |
| 4 | 60.0° C. | 01:00 | | — |
| 5 | 72.0° C. | 00:30 | | — |
| 6 | GOTO 3 | 4 more times | — | — |
| 7 | 95.0° C. | 00:10 | 40 | — |
| 8 | 60.0° C. | 01:00 | | — |
| 9 | 63.0° C. | 0:01 | | Plate read |
| 10 | 66.0° C. | 0:01 | | Plate read |
| 11 | GOTO 7 | 40 more times | — | — |
| 12 | 55.0° C. | 0:30 | — | — |

The periods of time at cycles 1-5 (steps 3-6) were set to be longer than those of other cycles after cycle 6 for activation of an initial reaction. The signal values at cycles 1-5 were detected and processed as RFU 0. The signal values at cycles 6-45 (steps 7-11) were detected at 63° C. and 66° C. The signal values were measured in Cal Red 610 channel.

Obtaining Signal-Change Values

The signal-change values were obtained by subtracting signal values at 66° C. from signal values at 63° C. at each of cycles 6-45.

Obtaining a Data Set of Cycle/Signal-Change Value

Using the signal-change values at cycles 6-45, a data set of cycle/signal-change value was obtained and plotted with cycles versus signal-change values.

Determination of the Presence or Absence of Target Nucleic Acid Sequence

The presence or absence of the target nucleic acid sequence was determined by fitting the data set of cycle/signal-change value with a sigmoidal function and applying a threshold value (RFU 110) to the fitted data set.

Figure 7:
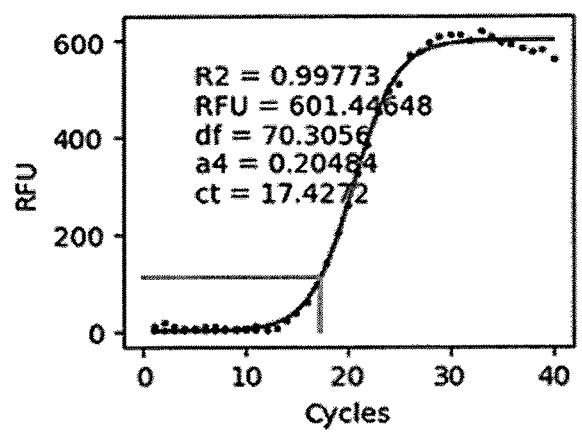
FIG. 7 represents amplification curves obtained by plotting data sets of cycle/signal-change value for a single target nucleic acid sequence.
Figure 7:
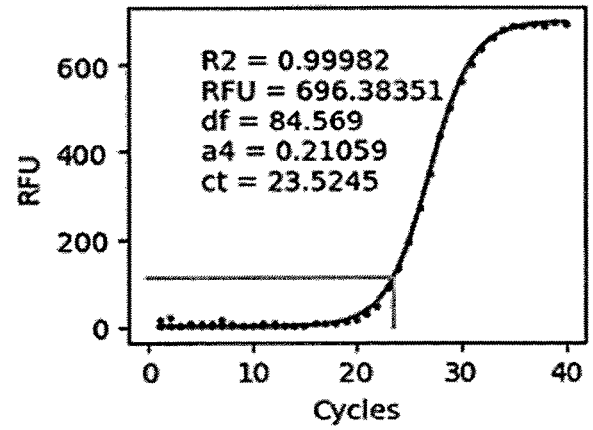
Figure 7:
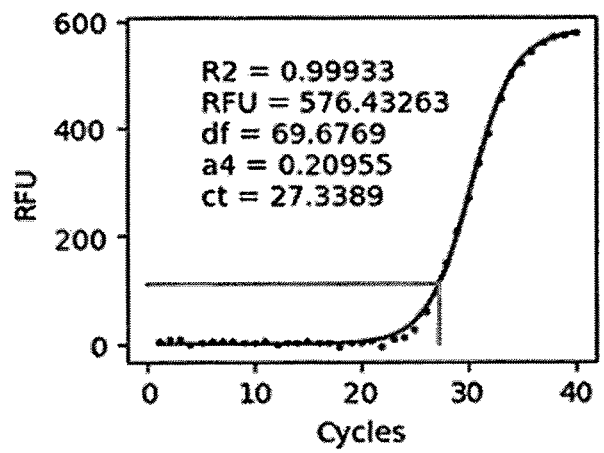
Figure 7:
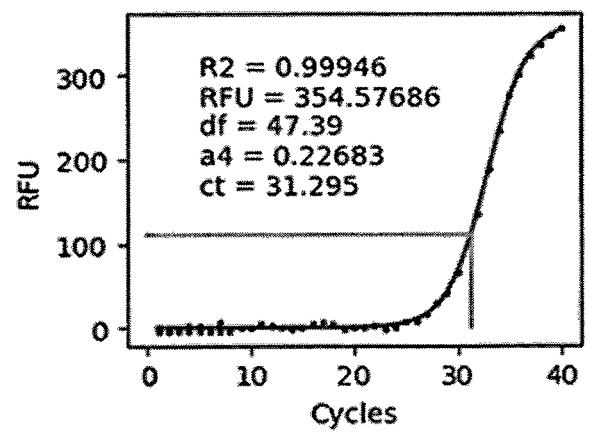

FIG. 7 represents amplification curves obtained by plotting data sets of cycle/signal-change value for the four samples. The dotted lines represent signal-change values calculated at each cycle and the solid lines represent sigmoidal-fitted values using a sigmoidal function of Mathematical Formula 1: RFU, the maximum signal value of the sigmoidal function; df, the maximum slope of the sigmoidal function; a4, a shape of the sigmoidal function; and Ct, a cycle at which the sigmoidal function crosses with the threshold value.

Where the amount of the CT pDNA was $10^6$ copies/reaction, $R^2$, the maximum signal value (RFU), df, a4 and Ct were analyzed to be 0.99773, 601.44648, 70.3056, 0.20484 and 17.4272, respectively. Where the amount of the CT pDNA was $10^4$ copies/reaction, $R^2$, the maximum signal value (RFU), df, a4 and Ct were analyzed to be 0.99982, 696.38351, 84.569, 0.21059 and 23.5245. Where the amount of the CT pDNA was $10^3$ copies/reaction, $R^2$, the maximum signal value (RFU), df, a4 and Ct were analyzed to be 0.99933, 576.43263, 69.6769, 0.20955 and 27.3389. Where the amount of the CT pDNA was $10^2$ copies/reaction, $R^2$, the maximum signal value (RFU), df, a4 and Ct were analyzed to be 0.99946, 354.57686, 47.39, 0.22683 and 31.295.

As a results, the four samples were analyzed to have the maximum values of the sigmoidal-fitted curves above the threshold value, RFU 110 and therefore to be positive for CT. In addition, as the amounts of the target nucleic acid sequence were decreased, the Ct values were measured to be increased (17.4272, 23.5245, 27.3389 and 31.295).

These results demonstrate that the present invention permits to determine the presence or absence of target nucleic acid sequences in an accurate and reliable manner by a data set of cycle/signal-change value obtained from a signal-change value at each amplification cycle.

Example 2: Detection of Target Nucleic Acid Sequence (Multiple Targets)

Example 2 exemplified an embodiment of the present invention in which two detection temperatures were determined based on an expected $T_m$ value of a duplex for a target nucleic acid sequence and used as reference temperatures.

Preparation of Signal-Generating Composition

Five samples each was mixed with signal-generating compositions contained in Allplex™ STI-GU kit (Seegene Inc., Cat. No. SD9802X) to detect *Chlamydia trachomatis* serovars L (CT) and *Treponema pallidum* (TP).

The expected $T_m$ of the extended duplex in the presence of CT is 64.5° C. The templating portion of the CTO for CT has a dual label of Cal Red 610 and BHQ2. The expected $T_m$ of the extended duplex in the presence of TP is 76° C. The templating portion of the CTO for TP also has a dual label of Cal Red 610 and BHQ2.

The five samples were prepared to contain pDNA molecules of CT and TP as Table 2.

TABLE 2

| Targets | CT (copies/rxn) | CT (copies/rxn) | CT (copies/rxn) |
|---|---|---|---|
| TP (copies/rxn) | CT $10^4$ <br> TP $10^4$ | CT $10^3$ <br> TP $10^4$ | CT $10^2$ <br> TP $10^4$ |
| TP (copies/rxn) | CT $10^4$ <br> TP $10^3$ | — | — |
| TP (copies/rxn) | CT $10^4$ <br> TP $10^2$ | — | — |

The reaction mixture for a real-time PCR amplification was prepared with Allplex™ STI-GU kit: Reaction mixture in the final volume of 20 µl containing 5 µl of 4×GU MOM, 5 µl of EM1, 5 µl of RNase-free Water and 5 µl of pDNA sample.

Reaction and Obtaining Signal Values

Real-time PCR amplification reactions were carried out using the five reaction mixtures on CFX96 (Ver. 1.6, Bio-Rad, Inc.). The temperature and time profiles of the amplification reactions are summarized in Table 3.

TABLE 3

| Step | Temp. | Time (min:sec) | Cycle | Plate read |
|---|---|---|---|---|
| 1 | 50.0° C. | 4:00 | 1 | — |
| 2 | 95.0° C. | 15:00 | 1 | — |
| 3 | 95.0° C. | 00:30 | 5 | — |
| 4 | 60.0° C. | 01:00 | | — |
| 5 | 72.0° C. | 00:30 | | — |
| 6 | GOTO 3 | 4 more times | — | — |
| 7 | 95.0° C. | 00:10 | 40 | — |
| 8 | 60.0° C. | 01:00 | | — |
| 9 | 63.0° C. | 0:01 | | Plate read |
| 10 | 66.0° C. | 0:01 | | Plate read |

TABLE 3-continued

| Step | Temp. | Time (min:sec) | Cycle | Plate read |
|---|---|---|---|---|
| 11 | 72.0° C. | 0:10 | — | — |
| 12 | 74.5° C. | 0:01 | | Plate read |
| 13 | 77.5° C. | 0:01 | | Plate read |
| 14 | GOTO 7 | 40 more times | — | — |
| 15 | 55.0° C. | 0:30 | — | |

The periods of time at cycles 1-5 (steps 3-6) were set to be longer than those of other cycles after cycle 6 for activation of an initial reaction. The signal values at cycles 1-5 were detected and processed as RFU 0. The signal values at cycles 6-45 (steps 7-14) were detected at detection temperatures. For CT detection, signal values were measured at 63° C. and 66° C. and for TP detection, signal values were measured at 74.5° C. and 77.5° C.

Obtaining Signal-Change Values

The signal-change values were obtained by difference of signal values at each of cycles 6-45. The signal-change values for detection of CT were obtained by subtracting signal values at 66° C. from signal values at 63° C., and the signal-change values for detection of TP were obtained by subtracting signal values at 77.5° C. from signal values at 74.5° C.

Obtaining a Data Set of Cycle/Signal-Change Value

Using the signal-change values at cycles 6-45, data sets of cycle/signal-change value was obtained and plotted with cycles versus signal-change values.

Determination of the Presence or Absence of Target Nucleic Acid Sequence

The presence or absence of the target nucleic acid sequence was determined by fitting the data sets of cycle/signal-change value with a sigmoidal function and applying a threshold value (RFU 110) to the fitted data set.

FIGS. 8-12 represent amplification curves obtained by plotting data sets of cycle/signal-change value for the five samples. The dotted lines represent signal-change values calculated at each cycle and the solid lines represent sigmoidal-fitted values using a sigmoidal function of Mathematical Formula 1. In FIGS. 8-12, the left curve represents an amplification curve for CT and the right curve represents an amplification curve for TP.

The five samples were analyzed to have the maximum values of the sigmoidal-fitted curves above the threshold value, RFU 110 and therefore to be positive for both CT and TP. These results address that where multiple target nucleic acid sequences are present, the present invention permits to determine the presence or absence of multiple target nucleic acid sequences in a simultaneous and accurate manner by a data set of cycle/signal-change value obtained from a signal-change value at each amplification cycle.

Figure 8:
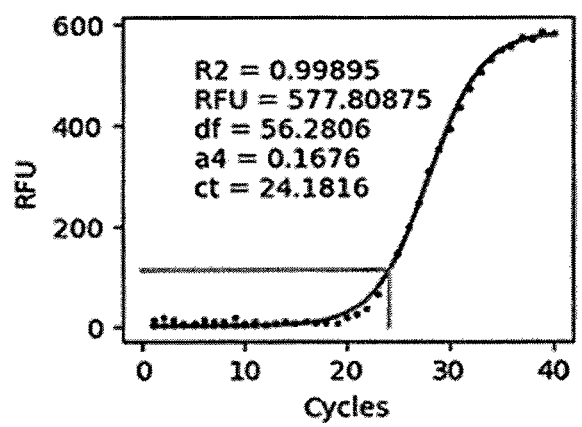
FIGS. 8-12 represent amplification curves obtained by plotting data sets of cycle/signal-change value for multiple target nucleic acid sequences.
Figure 8:
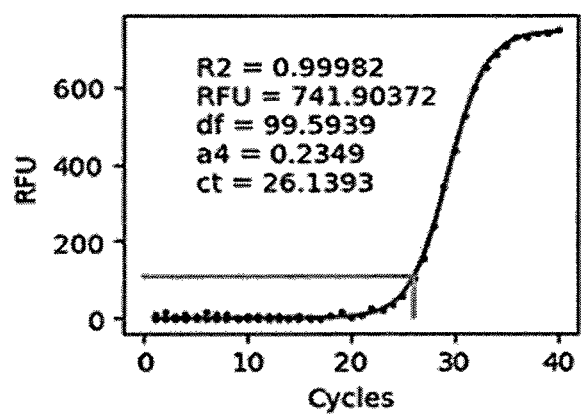
Figure 9:
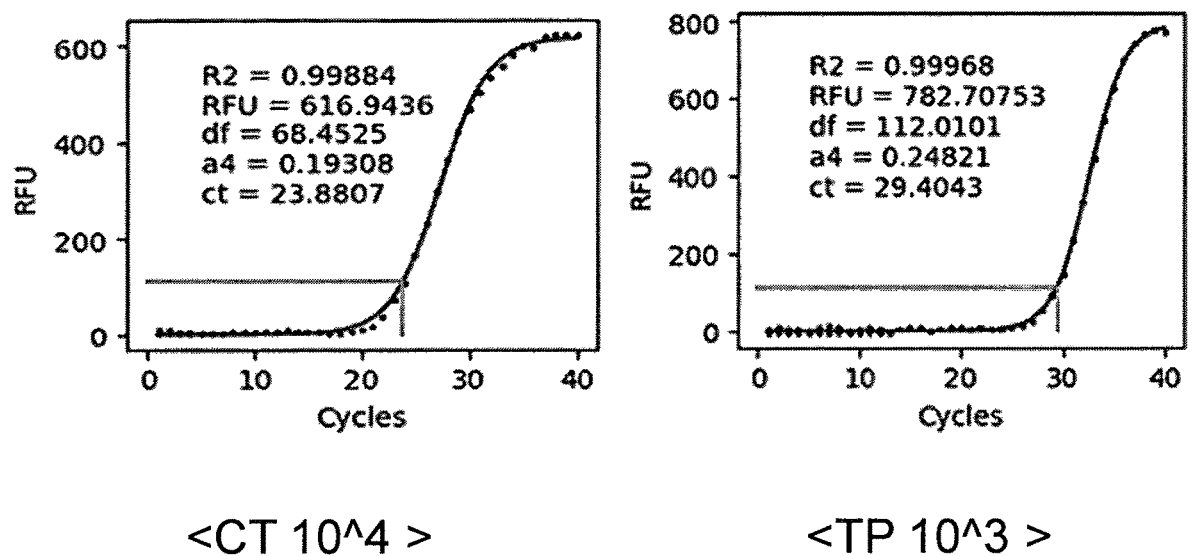
Figure 10:
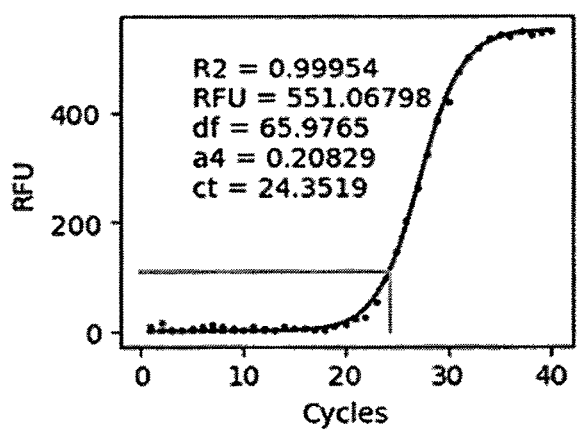
Figure 10:
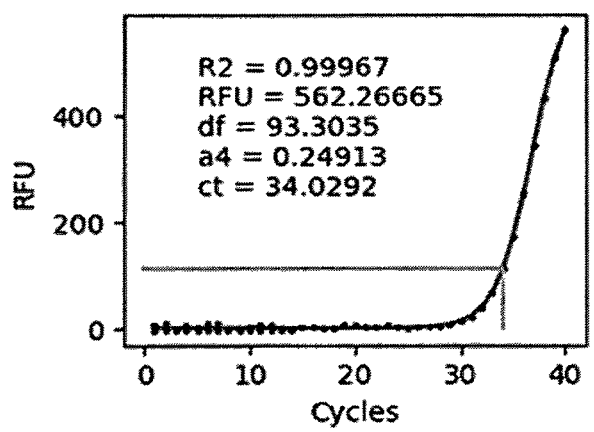
Figure 11:
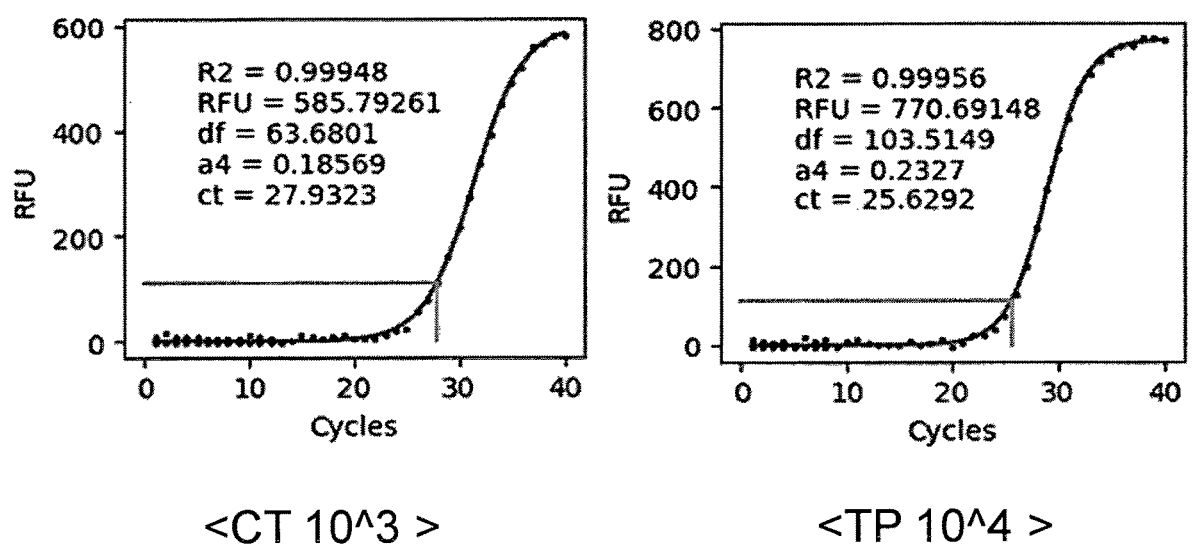
Figure 12:
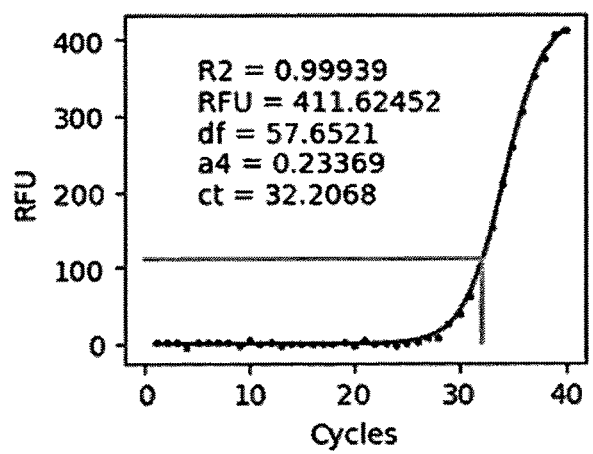
Figure 12:
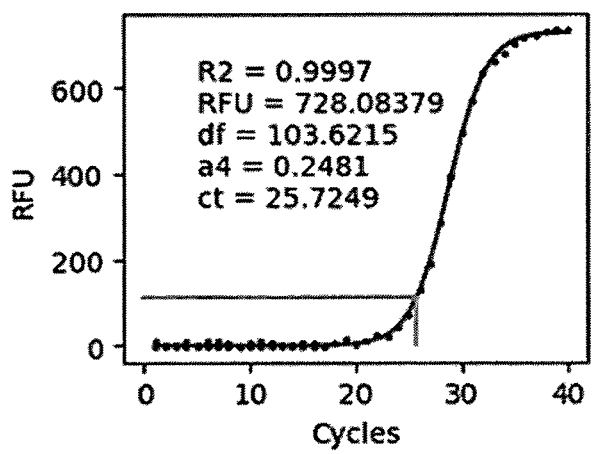

In addition, as the amounts of the target nucleic acid sequences in the five samples were decreased, the Ct values were measured to be increased. In FIGS. 8-10, as the amounts of the TP pDNA were decreased ($10^4$ copies/reaction, $10^3$ copies/reaction and $10^2$ copies/reaction) in the present of CP $10^4$ copies/reaction, Ct values were analyzed to be increased (26.1393, 29.4043 and 34.0292); and in FIGS. 8, 11 and 12, as the amounts of the CT pDNA were decreased ($10^4$ copies/reaction, $10^3$ copies/reaction and $10^2$ copies/reaction) in the present of TP $10^4$ copies/reaction, Ct values were analyzed to be increased (24.1816, 27.9323 and 32.2068).

Consequently, we have found that the present invention permits to simultaneously and reliably determine the presence or absence of multiple target nucleic acid sequences in a single reaction vessel by a data set of cycle/signal-change value obtained from a signal-change value at each amplification cycle.

Example 3: Detection of Target Nucleic Acid Sequence Using Reference Temperatures Selected from More than Three Detection Temperatures In Examples 1-2, two detection temperatures were determined based on an expected $T_m$ value of a duplex for a target nucleic acid sequence and used as reference temperatures. Example 3 exemplified an embodiment of the present invention in which at least three detection temperatures were determined for each target nucleic acid sequence to obtain signal values and then two reference temperatures were selected among the at least three detection temperatures by considering the signal values.

Preparation of Signal-Generating Composition

Sixteen samples each was mixed with signal-generating compositions contained in AnyplexII™ HPV HR kit (Seegene Inc., Cat. No. HP7E00X) to detect the HBB (hemoglobin beta) gene, HPV (human papillomavirus) type 35 and HPV type 18.

The signal-generating composition contains a composition for forming a duplex providing a detectable signal for a target nucleic acid sequence by the PTOCE method. Where the target nucleic acid sequence is present in a sample, a mediation oligonucleotide (i.e., PTO) specifically hybridized with the target nucleic acid sequence is cleaved by a polymerase having 5'-nuclease activity and a cleavage fragment is hybridized with a capture oligonucleotide CTO) to be extended, thereby forming an extended duplex providing a detectable signal.

The expected $T_m$ of the extended duplex in the presence of the HBB gene is 63° C. The templating portion of the CTO for the HBB gene has a dual label of Q670 and BHQ2. The expected $T_m$ of the extended duplex in the presence of HPV type 35 is 70.5° C. The templating portion of the CTO for HPV type 35 has a dual label of Q670 and BHQ2. The expected $T_m$ of the extended duplex in the presence of HPV type 18 is 76.5° C. The templating portion of the CTO for HPV type 18 has a dual label of Q670 and BHQ2.

The sixteen samples were prepared as Table 4 using pDNA cloned with the HBB gene, the HPV type 35 sequence or the HPV type 18 sequence in the amount of 50 copies/reaction.

TABLE 4

| Samples | 1 | 2 | 3 | 4 |
|---|---|---|---|---|
| A | — | — | HBB | HBB |
| | — | HPV type 35 | — | HPV type 35 |
| | — | — | — | — |
| | — | — | — | — |
| B | — | — | HBB | HBB |
| | — | HPV type 35 | — | HPV type 35 |
| | — | — | — | — |
| C | — | — | HBB | HBB |
| | — | HPV type 35 | — | HPV type 35 |
| | HPV type 18 | HPV type 18 | HPV type 18 | HPV type 18 |
| D | — | — | HBB | HBB |
| | — | HPV type 35 | — | HPV type 35 |
| | HPV type 18 | HPV type 18 | HPV type 18 | HPV type 18 |

The reaction mixture for a real-time PCR amplification was prepared with AnyplexII™ HPV HR kit: Reaction mixture in the final volume of 20 μl containing 5 μl of 4×HPV HR TOM, 5 μl of EM1, 5 μl of RNase-free Water and 5 µl of pDNA sample. TOM is an oligonucleotide mixture and EM1 is Taq polymerase.

Reaction

Real-time PCR amplification reactions were carried out using the sixteen reaction mixtures on CFX96 (Ver. 1.6, Bio-Rad, Inc.) and signals were detected in a channel (Q670 channel). The temperature and time profiles of the amplification reactions are summarized in Table 5.

TABLE 5

| Step | Temp. | Time (min:sec) | Cycle | Plate read |
|---|---|---|---|---|
| 1 | 95° C. | 15:00 | — | — |
| 2 | 95° C. | 00:03 | 25 | — |
| 3 | 60° C. | 00:10 | — | — |
| 4 | 72° C. | 00:10 | — | — |
| 5 | 95° C. | 00:03 | — | — |
| 6 | 60° C. | 00:10 | — | — |
| 7 | 60° C. | 00:01 | — | Plate read |
| 8 | 61.5° C. | 00:01 | — | Plate read |
| 9 | 63° C. | 00:01 | — | Plate read |
| 10 | 64.5° C. | 00:01 | — | Plate read |
| 11 | 66° C. | 00:01 | — | Plate read |
| 12 | 67.5° C. | 00:01 | — | Plate read |
| 13 | 69° C. | 00:01 | — | Plate read |
| 14 | 70.5° C. | 00:01 | — | Plate read |
| 15 | 72° C. | 00:01 | — | Plate read |
| 16 | 73.5° C. | 00:01 | — | Plate read |
| 17 | 75° C. | 00:01 | — | Plate read |
| 18 | 76.5° C. | 00:01 | — | Plate read |
| 19 | 78° C. | 00:01 | — | Plate read |
| 20 | 79.5° C. | 00:01 | — | Plate read |
| 21 | 81° C. | 00:01 | — | Plate read |
| 22 | GOTO 2 | 24 more times | — | — |
| 23 | 55° C. | 00:30 | — | — |

The amplification reactions were performed for 50 cycles. Steps 2-4 correspond to cycles in odd number and steps 5-21 correspond to cycles in even number. The signal values were measured only at cycles in even number.

Obtaining Signal Values at Detection Temperatures

For each target nucleic acid sequence, six detection temperatures were set in a detection temperature range including an expected $T_m$ value of a duplex for a corresponding target nucleic acid sequence. For the HBB gene, the detection temperatures were set 60° C., 61.5° C., 63° C., 64.5° C., 66° C. and 67.5° C.; for the HPV type 35 sequence, the detection temperatures were set 66° C., 67.5° C., 69° C., 70.5° C., 72° C. and 73.5° C.; and for the HPV type 18 sequence, the detection temperatures were set 73.5° C., 75° C., 76.5° C., 78° C., 79.5° C. and 81° C. The detection temperatures were set in the interval of 1.5° C.

Signal values at cycles in odd number were approximated by interpolation of those at cycles in even number. In this Example, an average value of signal values at adjacent cycles in even number was determined as signal values at cycles in odd number.

The temperatures between detection temperatures and signal values at the temperatures between detection temperatures were approximated by interpolation of detection temperatures and signal values at detection temperatures. In this Example, an average value of signal values at adjacent detection temperatures was determined as signal values at an average temperature of adjacent detection temperatures.

Selection of Reference Temperatures

The reference temperatures for target nucleic acid sequences were selected as follows:

For selection of the reference temperatures, signal values at cycles 46-50 were used. Five signal-change values were calculated using signal values measured at six detection temperatures at each cycle for the HBB gene. The signal-change values were calculated by subtraction of signal values at adjacent detection temperatures and assigned to interpolated temperatures of the adjacent detection temperatures (i.e., an average temperature of the two adjacent detection temperatures). The average values of the signal-change values at the same detection temperature at cycles 46-50 were calculated to give average signal-change values at corresponding detection temperatures. The highest average signal-change value was assigned as a first average signal-change value, a higher average signal-change value among adjacent average signal-change values to the highest average signal-change value was assigned as a second average signal-change value and the other average signal-change value assigned as a third average signal-change value. The ratio of (difference between the second average signal-change value and the third average signal-change value) to (difference between the first average signal-change value and the third average signal-change value) was calculated. Where the ratio exceeded a threshold value (0.4), the highest average signal-change value is assigned at a median temperature between the temperature for the first average signal-change value and the temperature for the second average signal-change value, and two temperatures being apart from the median temperature in the same interval (e.g., 1.5° C.) are selected in both directions as two reference temperatures. Where the ratio is no more than the threshold value (0.4), the first average signal-change value is finally determined to be a highest average signal-change value and two temperatures being apart from an interpolated temperature corresponding to the first average signal-change value in the same interval (e.g., 1.5° C.) are selected in both directions as two reference temperatures.

Two reference temperatures for detection of HPV type 35 and HPV type 18 were selected using signal values at six detection temperatures at cycles 46-50 in the same manner as those for the HBB gene.

Table 6 shows two reference temperatures for each sample, which were used to calculate signal-change values for detection of the HBB gene.

TABLE 6

| Samples | 1 | 2 | 3 | 4 |
|---|---|---|---|---|
| A | — | — | 62.25° C. | 62.25° C. |
|   |   |   | 65.25° C. | 65.25° C. |
| B | — | — | 61.50° C. | 61.50° C. |
|   |   |   | 64.50° C. | 64.50° C. |
| C | — | — | 62.25° C. | 61.50° C. |
|   |   |   | 65.25° C. | 64.50° C. |
| D | — | — | 62.25° C. | 62.25° C. |
|   |   |   | 65.25° C. | 65.25° C. |

We expected that two detection temperatures for the HBB gene were 61.5° C. and 64.5° C. based on an expected $T_m$ (63° C.) of a duplex for the HBB gene. In samples B3, B4 and C4, two detection temperatures were the same as the expected two detection temperatures based on the expected $T_m$. In samples A3, A4, C3, D3 and D4, the selected two detection temperatures were 62.25° C. and 65.25° C. Signal values at 62.25° C. and 65.25° C. were obtained by interpolation of signal values at adjacent detection temperatures.

Table 7 shows two reference temperatures for each sample, which were used to calculate signal-change values for detection of the HPV type 35 sequence.

TABLE 7

| Samples | 1 | 2 | 3 | 4 |
|---|---|---|---|---|
| A | — | 69.75° C. 72.75° C. | — | 69.75° C. 72.75° C. |
| B | — | 69.75° C. 72.75° C. | — | 69.75° C. 72.75° C. |
| C | — | 69.75° C. 72.75° C. | — | 69.75° C. 72.75° C. |
| D | — | 69.75° C. 72.75° C. | — | 69.75° C. 72.75° C. |

We expected that two detection temperatures for the HPV type 35 sequence were 69° C. and 72° C. based on an expected $T_m$ (70.5° C.) of a duplex for the HPV type 35 sequence. In all samples, two detection temperatures were selected as 69.75° C. and 72.75° C. Signal values at 69.75° C. and 72.75° C. were obtained by interpolation of signal values at adjacent detection temperatures.

Table 8 shows two reference temperatures for each sample, which were used to calculate signal-change values for detection of the HPV type 18 sequence.

TABLE 8

| Samples | 1 | 2 | 3 | 4 |
|---|---|---|---|---|
| A | — | — | — | — |
| B | — | — | — | — |
| C | 75.75° C. 78.75° C. | 75.75° C. 78.75° C. | 75.75° C. 78.75° C. | 75.75° C. 78.75° C. |
| D | 75.75° C. 78.75° C. | 75.75° C. 78.75° C. | 75.75° C. 78.75° C. | 75.75° C. 78.75° C. |

We expected that two detection temperatures for the HPV type 18 sequence were 75° C. and 78° C. based on an expected $T_m$ (76.5° C.) of a duplex for the HPV type 18 sequence. In all samples, two detection temperatures were selected as 75.75° C. and 78.75° C. Signal values at 75.75° C. and 78.75° C. were obtained by interpolation of signal values at adjacent detection temperatures.

Obtaining a Data Set of Cycle/Signal-Change Value

The signal-change values for each sample and target nucleic acid sequence were calculated by subtraction of signal values at the selected two reference temperatures.

Determination of the Presence or Absence of Target Nucleic Acid Sequence

The presence or absence of the target nucleic acid sequences in sixteen samples was determined by fitting the data sets of cycle/signal-change value with a sigmoidal function and applying a threshold value (RFU 50) to the fitted data set.

Tables 9-11 represent $C_t$ values of the target nucleic acid sequences in the samples.

TABLE 9

| | HBB | | | |
|---|---|---|---|---|
| Samples | 1 | 2 | 3 | 4 |
| A | — | — | 35.70 | 37.86 |
| B | — | — | 35.67 | 39.79 |
| C | — | — | 36.76 | 39.21 |
| D | — | — | 37.16 | 39.98 |

TABLE 10

| | HPV type 35 | | | |
|---|---|---|---|---|
| Samples | 1 | 2 | 3 | 4 |
| A | — | 35.84 | — | 35.77 |
| B | — | 36.24 | — | 35.45 |
| C | — | 35.26 | — | 36.22 |
| D | — | 35.60 | — | 34.91 |

TABLE 11

| | HPV type 18 | | | |
|---|---|---|---|---|
| Samples | 1 | 2 | 3 | 4 |
| A | — | — | — | — |
| B | — | — | — | — |
| C | 34.40 | 34.10 | 34.15 | 34.71 |
| D | 33.43 | 35.00 | 34.20 | 34.61 |

The results demonstrate that reference temperatures can be selected from at least three detection temperatures in considering signal values at at least three detection temperatures and the presence or absence of target nucleic acid sequences can be determined by signal-change values between the selected reference temperatures at amplification cycles.

Expected or calculated $T_m$ values of duplexes for target nucleic acid sequences would be different from real reaction $T_m$ values under reaction conditions such as types of samples, reaction temperatures, salt concentrations, divalent cation concentrations, oligonucleotide concentrations and pH. Therefore, real reaction $T_m$ values of duplexes for target nucleic acid sequences would have reaction-to-reaction variation. The present invention using reference temperatures determined by considering signal values of detection temperatures is very advantageous in detecting target nucleic acid sequences accurately in the sense that reference temperatures suitable to real reaction $T_m$ values are selected.

Example 4: Detection of Target Nucleic Acid Sequence Using Reference Temperatures Selected from More than Three Detection Temperatures Another embodiment of the present invention using reference temperatures selected from more than three detection temperatures was exemplified with different target nucleic acid sequences and duplexes comprising a different reporter label from those used in Example 3.

Preparation of Signal-Generating Composition

Sixteen samples each was mixed with signal-generating compositions to detect the HPV (human papillomavirus) type 33, HPV type 39 and HPV type 52. The signal-generating compositions contain a composition for forming a duplex providing a detectable signal for a target nucleic acid sequence by the PTOCE method.

The expected $T_m$ of the extended duplex in the presence of the HPV type 33 is 63° C. The templating portion of the CTO for the HPV type 33 has a dual label of Cal red 610 and BHQ2. The expected $T_m$ of the extended duplex in the presence of HPV type 39 is 70° C. The templating portion of the CTO for HPV type 39 has a dual label of Cal red 610 and BHQ2. The expected $T_m$ of the extended duplex in the presence of HPV type 52 is 76° C. The templating portion of the CTO for HPV type 52 has a dual label of Cal red 610 and BHQ2.

The sixteen samples were prepared as Table 12 using pDNA cloned with the HPV type 33 sequence, the HPV type 39 sequence or the HPV type 52 sequence in the amount of 50 copies/reaction.

TABLE 12

| Samples | 1 | 2 | 3 | 4 |
|---|---|---|---|---|
| A | — | — | HPV type 33 | HPV type 33 |
|   | — | HPV type 39 | — | HPV type 39 |
|   | — | — | — | — |
| B | — | — | HPV type 33 | HPV type 33 |
|   | — | HPV type 39 | — | HPV type 39 |
|   | — | — | — | — |
| C | — | — | HPV type 33 | HPV type 33 |
|   | — | HPV type 39 | — | HPV type 39 |
|   | HPV type 52 | HPV type 52 | HPV type 52 | HPV type 52 |
| D | — | — | HPV type 33 | HPV type 33 |
|   | — | HPV type 39 | — | HPV type 39 |
|   | HPV type 52 | HPV type 52 | HPV type 52 | HPV type 52 |

The sequences of the upstream primer, downstream primer, PTO and CTO used in this Example are:

33-F
(SEQ ID NO: 1)
5'-AATGGTATTTGTTGGGGCAATIIIIIATTTGTTAC-3'

33-R
(SEQ ID NO: 2)
5'-TCCTGIAAACTASCAGATGGAGGIIIIITTAAACCAA-3'

33-PTO
(SEQ ID NO: 3)
5'-AACGGTACGACGGCACACARGTAACTAGTGACAGTACATATAAAAAT GA[C3 spacer]-3'

33-CTO
(SEQ ID NO: 4)
5'-[BHQ2]TTATATTTTATTTTATTATA[T(CAL Red 610)]ACTGC CGTCGTACCGTT-3'

39-F
(SEQ ID NO: 5)
5'-GAYACTACCCGTAGTACCAACTTTACIIIIICTACCTCTA-3'

39-R
(SEQ ID NO: 6)
5'-CTGGCAGATGGTGGAGGAGIIIIIGCRAAATTC-3'

39-PTO
(SEQ ID NO: 7)
5'-ACGGCGCAATACCTCCTCCACGTGCCTKRTATATTCCTTAAA[C3 spacer]-3'

39-CTO
(SEQ ID NO: 8)
5'-[BHQ2]TATTATTATTAAGAGCTGCT[T(CAL Red 610)]CCGAG GTATTGCGCCGT-3'

52-F
(SEQ ID NO: 9)
5'-CAGGGCCACAATAATGGCAIIIIITGGGGCAAT-3

52-R
(SEQ ID NO: 10)
5'-CCTTTCCTTTAGGTGGTGTGTIIIIIITGACAWGT-3'

52-PTO
(SEQ ID NO: 1)
5'-TGTCGATCGCGTCCAGTCCTCTAAAATAGTGGCATCCATYTTAT [C3 spacer]-3'

52-CTO
(SEQ ID NO: 12)
5'-[BHQ2]TGCGATATGTCGGGTACGAC[T(CAL Red 610)]GGTGG ACGCGATCGACA-3'

(I: Deoxyinosine)
(Underlined letters indicate the 5'-tagging portion of PTO)

The reaction mixture for a real-time PCR amplification was prepared to contain, in the final volume of 20 μl, a sample, oligonucleotides for HPV type 33 target detection [6 pmole of forward primer (SEQ ID NO: 1), 6 pmole of reverse primer (SEQ ID NO: 2), 3 pmole of PTO (SEQ ID NO: 3), 1 pmole of CTO (SEQ ID NO: 4)], oligonucleotides for HPV type 39 target detection [4 pmole of forward primer (SEQ ID NO: 5) and 4 pmole of reverse primer (SEQ ID NO: 6), 3 pmole of PTO (SEQ ID NO: 7), 1 pmole of CTO (SEQ ID NO: 8)], oligonucleotides for HPV type 52 target detection [3 pmole of forward primer (SEQ ID NO: 9) and 3 pmole of reverse primer (SEQ ID NO: 10), 2 pmole of PTO (SEQ ID NO6: 11), 1 pmole of cm (SEQ ID NO: 12)], and 10 μl of EM4 (Taq polymerase).

Reaction

Real-time PCR amplification reactions were carried out using the sixteen reaction mixtures on CFX96 (Ver. 1.6, Bio-Rad, Inc.) and signals were detected in a channel (Cal red 610 channel). The temperature and time profiles of the amplification reactions are the same as the profiles in Example 3.

Obtaining Signal Values at Detection Temperatures

For each target nucleic acid sequence, six detection temperatures were set in a detection temperature range including an expected $T_m$ value of a duplex for a corresponding target nucleic acid sequence. For the HPV type 33 gene, the detection temperatures were set 60° C., 61.5° C., 63° C., 64.5° C., 66° C. and 67.5° C.; for the HPV type 39 sequence, the detection temperatures were set 66° C., 67.5° C., 69° C., 70.5° C., 72° C. and 73.5° C.; and for the HPV type 52 sequence, the detection temperatures were set 73.5° C., 75° C., 76.5° C., 78° C., 79.5° C. and 81° C. The detection temperatures were set in the interval of 1.5° C.

Signal values at cycles in odd number were approximated by interpolation of those at cycles in even number. In this Example, an average value of signal values at adjacent cycles in even number was determined as signal values at cycles in odd number.

The temperatures between detection temperatures and signal values at the temperatures between detection temperatures were approximated by interpolation of detection temperatures and signal values at detection temperatures. In this Example, an average value of signal values at adjacent detection temperatures was determined as signal values at an average temperature of adjacent detection temperatures.

Selection of Reference Temperatures

The reference temperatures for target nucleic acid sequences were selected as described in Example 3.

Table 13 shows two reference temperatures for each sample, which were used to calculate signal-change values for detection of the HPV type 33.

TABLE 13

| Samples | 1 | 2 | 3 | 4 |
|---|---|---|---|---|
| A | — | — | 62.25° C. | 62.25° C. |
|   |   |   | 65.25° C. | 65.25° C. |
| B | — | — | 62.25° C. | 62.25° C. |
|   |   |   | 65.25° C. | 65.25° C. |

TABLE 13-continued

| Samples | 1 | 2 | 3 | 4 |
|---|---|---|---|---|
| C | — | — | 62.25° C. | 63.00° C. |
|   |   |   | 65.25° C. | 66.00° C. |
| D | — | — | 62.25° C. | 63.00° C. |
|   |   |   | 65.25° C. | 66.00° C. |

We expected that two detection temperatures for the HPV type 33 were 61.5° C. and 64.5° C. based on an expected $T_m$ (63° C.) of a duplex for the HPV type 33. In samples A3, B3, C3, D3, A4 and B4, the selected two detection temperatures were 62.25° C. and 65.25° C. In samples C4 and D4, the selected two detection temperatures were 63° C. and 66° C. Signal values at 62.25° C. and 65.25° C. were obtained by interpolation of signal values at adjacent detection temperatures.

Table 14 shows two reference temperatures for each sample, which were used to calculate signal-change values for detection of the HPV type 39 sequence.

TABLE 14

| Samples | 1 | 2 | 3 | 4 |
|---|---|---|---|---|
| A | — | 69.00° C. | — | 69.00° C. |
|   |   | 72.00° C. |   | 72.00° C. |
| B | — | 69.00° C. | — | 69.00° C. |
|   |   | 72.00° C. |   | 72.00° C. |
| C | — | 69.00° C. | — | 69.00° C. |
|   |   | 72.00° C. |   | 72.00° C. |
| D | — | 69.00° C. | — | 69.00° C. |
|   |   | 72.00° C. |   | 72.00° C. |

We expected that two detection temperatures for the HPV type 39 sequence were 69° C. and 72° C. based on an expected $T_m$ (70° C.) of a duplex for the HPV type 39 sequence. In all samples, two detection temperatures were selected as 69° C. and 72° C. Table 15 shows two reference temperatures for each sample, which were used to calculate signal-change values for detection of the HPV type 52 sequence.

TABLE 15

| Samples | 1 | 2 | 3 | 4 |
|---|---|---|---|---|
| A | — | — | — | — |
| B | — | — | — | — |
| C | 75.75° C. | 75.75° C. | 75.75° C. | 75.75° C. |
|   | 78.75° C. | 78.75° C. | 78.75° C. | 78.75° C. |
| D | 75.75° C. | 75.75° C. | 75.75° C. | 75.75° C. |
|   | 78.75° C. | 78.75° C. | 78.75° C. | 78.75° C. |

We expected that two detection temperatures for the HPV type 52 sequence were 75° C. and 78° C. based on an expected $T_m$ (76° C.) of a duplex for the HPV type 52 sequence. In all samples, two detection temperatures were selected as 75.75° C. and 78.75° C. Signal values at 75.75° C. and 78.75° C. were obtained by interpolation of signal values at adjacent detection temperatures.

Obtaining a Data Set of Cycle/Signal-Change Value

The signal-change values for each sample and target nucleic acid sequence were calculated by subtraction of signal values at the selected two reference temperatures.

Determination of the Presence or Absence of Target Nucleic Acid Sequence

The presence or absence of the target nucleic acid sequences in sixteen samples was determined by fitting the data sets of cycle/signal-change value with a sigmoidal function and applying a threshold value (RFU 50) to the fitted data set.

Tables 16-18 represent $C_t$ values of the target nucleic acid sequences in the samples.

TABLE 16

| | HPV type 33 | | | |
|---|---|---|---|---|
| Samples | 1 | 2 | 3 | 4 |
| A | — | — | 37.51 | 39.12 |
| B | — | — | 36.70 | 39.90 |
| C | — | — | 40.17 | 40.49 |
| D | — | — | 38.84 | 41.47 |

TABLE 17

| | HPV type 39 | | | |
|---|---|---|---|---|
| Samples | 1 | 2 | 3 | 4 |
| A | — | 34.15 | — | 34.59 |
| B | — | 34.96 | — | 35.01 |
| C | — | 34.48 | — | 34.63 |
| D | — | 34.80 | — | 34.86 |

TABLE 18

| | HPV type 52 | | | |
|---|---|---|---|---|
| Samples | 1 | 2 | 3 | 4 |
| A | — | — | — | — |
| B | — | — | — | — |
| C | 35.07 | 33.88 | 34.53 | 35.81 |
| D | 32.74 | 35.58 | 34.75 | 34.72 |

The results demonstrate that reference temperatures can be selected from at least three detection temperatures in considering signal values at at least three detection temperatures and the presence or absence of target nucleic acid sequences can be determined by signal-change values between the selected reference temperatures at amplification cycles.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52 (e).

What is claimed is:

1. A method for detecting a plurality of target nucleic acid sequences in a sample, comprising:

contacting in a single reaction vessel the sample to signal-generating compositions for detecting the plurality of target nucleic acid sequences; wherein the signal-generating compositions form a plurality of duplexes for the plurality of target nucleic acid sequences, each of the plurality of duplexes provides a signal indicating the presence or absence of each corresponding target nucleic acid sequence and the plurality of duplexes have $T_m$ values different from each other;

performing a real-time amplification reaction for at least two cycles for (i) the formation of the plurality of duplexes and (ii) a hybridization and/or dissociation of the formed duplexes;

obtaining at all or partial cycles of the reaction, signal values at at least two detection temperatures in each of a plurality of detection temperature ranges assigned to the plurality of target nucleic acid sequences; wherein each of the plurality of detection temperature ranges comprises a temperature range in which the amount of a duplex for each corresponding target nucleic acid sequence is changed;

obtaining a signal-change value of signal values between two reference temperatures selected from the at least two detection temperatures in each of the plurality of detection temperature ranges such that a data set of cycle/signal-change value for each of the plurality of target nucleic acid sequences is obtained; and determining the presence or absence of the plurality of target nucleic acid sequences in the sample by the data set of cycle/signal-change value for each of the plurality of target nucleic acid sequences.

2. The method according to claim 1, wherein the signal-generating compositions comprise labeled oligonucleotides for formation of the plurality of duplexes each of which provides the signal indicating the presence of each corresponding target nucleic acid sequence, the formed duplexes comprise the labeled oligonucleotides and the hybridization and/or dissociation of the formed duplexes provides a detectable signal.

3. The method according to claim 1, wherein the duplexes comprise labeled oligonucleotides comprising a label having the same signal property.

4. The method according to claim 1, wherein the plurality of duplexes are (i) a duplex formed by hybridization between the target nucleic acid sequence and a labeled oligonucleotide, (ii) a duplex formed by hybridization between an oligonucleotide comprising a hybridizing sequence complementary to the target nucleic acid sequence and a labeled oligonucleotide complementary to at least a portion of the hybridizing sequence or (iii) a duplex formed in a dependent manner on a mediation oligonucleotide-involving cleavage wherein the mediation oligonucleotide is the hybridized with the target nucleic acid sequence.

5. The method according to claim 4, wherein the duplex formed in a dependent manner on the mediation oligonucleotide-involving cleavage is a duplex formed in a dependent manner on formation of an extended strand which is formed by extension of a fragment released by the mediation oligonucleotide-involving cleavage.

6. The method according to claim 4, wherein the duplex formed in a dependent manner on a mediation oligonucleotide-involving cleavage is a duplex formed by hybridization of a fragment released by the mediation oligonucleotide-involving cleavage with a counterpart oligonucleotide.

7. The method according to claim 4, wherein the duplex formed in a dependent manner on the mediation oligonucleotide-involving cleavage is a duplex formed in a dependent manner on formation of an extended strand by (i) hybridizing the mediation oligonucleotide with the target nucleic acid sequence, (ii) cleaving the mediation oligonucleotide or a mediation oligonucleotide-containing amplicon by a nuclease to generate a fragment, (iii) hybridizing the fragment with a capturing oligonucleotide comprising a 5'-capturing portion to be hybridized with the fragment and a 3'-templating portion and (iv) performing an extension reaction of the fragment hybridized with the capturing portion on the 3'-templating portion to form the extended strand.

8. The method according to claim 7, wherein the mediation oligonucleotide-containing amplicon is produced by amplifying the target nucleic acid sequence using the mediation oligonucleotide as a primer and cleaving a portion of a sequence complementary to the mediation oligonucleotide in the amplicon to release a fragment.

9. The method according to claim 4, wherein the duplex formed in a dependent manner on a mediation oligonucleotide-involving cleavage is a duplex formed by (i) hybridizing the mediation oligonucleotide with the target nucleic acid sequence, (ii) cleaving the mediation oligonucleotide by a nuclease to generate a fragment and (iii) hybridizing the fragment with a counterpart oligonucleotide.

10. The method according to claim 5, wherein the duplex formed in a dependent manner on formation of the extended strand is (i) a duplex between the extended strand and the capturing oligonucleotide, (ii) a duplex between the capturing oligonucleotide and a capturing oligonucleotide-hybridizing oligonucleotide, (iii) a duplex between an extended strand-capturing oligonucleotide and a dually extended strand from the extended strand captured to the extended strand-capturing oligonucleotide, (iv) a duplex between the dually extended strand and a dually extended strand-hybridizing oligonucleotide, or (v) a duplex between the extended strand-capturing oligonucleotide and an oligonucleotide to be hybridized with the extended strand-capturing oligonucleotide.

11. The method according to claim 1, wherein when temperatures and signal values thereof are interpolated from the at least two detection temperatures, the at least two detection temperatures comprise the interpolated detection temperatures.

12. The method according to claim 1, wherein the at least two detection temperatures are 2-10 in number.

13. The method according to claim 1, wherein the at least two detection temperatures are selected such that an expected Tm value of the duplex for each corresponding target nucleic acid sequence is encompassed between a highest detection temperature and a lowest detection temperature of the at least two detection temperatures.

14. The method according to claim 1, wherein when the at least two detection temperatures is two detection temperatures, the two detection temperatures are selected as the two reference temperatures.

15. The method according to claim 1, wherein the two reference temperatures are selected with a highest detection temperature and a lowest detection temperature of the at least two detection temperatures.

16. The method according to claim 1, wherein the two reference temperatures differ from each other by no more than 6° C.

17. The method according to claim 1, wherein the signal-change value is calculated by using all or partial signal values between the two reference temperatures.

18. The method according to claim 1, wherein the signal-change value is obtained by using two signal values at the two reference temperatures.

19. The method according to claim 1, wherein the at least two detection temperatures is no less than 3 in number; the method further comprises analyzing the signal values at the least three detection temperatures to select the two reference temperatures.

20. The method according to claim 1, wherein the at least two detection temperatures is no less than 3 in number; signal-change values are calculated by using signal values at the at least three detection temperatures to select the two reference temperatures.

21. The method according to claim 1, wherein the at least two detection temperatures is no less than 3 in number; signal-change values are calculated by using signal values at the at least three detection temperatures and the two reference temperatures are selected such that a highest signal-change value among the calculated signal-change values is included between the two reference temperatures.

22. The method according to claim 21, wherein the highest signal-change value is assigned to a temperature between the detection temperatures used for calculating the highest signal-change value.

23. The method according to claim 1, wherein the at least two detection temperatures is no less than 3 in number; signal-change values are calculated by using signal values between immediately adjacent detection temperatures and the two reference temperatures are selected such that a highest signal-change value among the calculated signal-change values is included between the two reference temperatures.

24. The method according to claim 23, wherein the highest signal-change value is assigned to a temperature between the detection temperatures used for calculating the highest signal-change value.

25. The method according to claim 23, wherein the signal-change values are assigned at temperatures between the detection temperatures used for calculating corresponding signal-change values; the highest signal-change value among the signal-change values is assigned as a first-change value, a higher signal-change value and a lower signal-change value among two signal-change values adjacent to the highest signal-change value are assigned as a second signal-change value and a third signal-change value, respectively; if the ratio of (i) difference between the second signal-change value and the third signal-change value to (ii) difference between the first signal-change value and the third signal-change value exceeds a threshold value, the highest signal-change value is assigned at a median temperature between the temperature for the first signal-change value and the temperature for the second signal-change value, and two temperatures being apart from the median temperature in the same interval are selected in both directions as the two reference temperatures.

26. The method according to claim 23, wherein the signal-change values are assigned at temperatures between the detection temperatures used for calculating corresponding signal-change values; a highest signal-change value among the signal-change values is assigned as a first-change value, a higher signal-change value and a lower signal-change value among two signal-change values adjacent to the highest signal-change value are assigned as a second signal-change value and a third signal-change value, respectively; if the ratio of (i) difference between the second signal-change value and the third signal-change value to (ii) difference between the first signal-change value and the third signal-change value is no more than a threshold value, the highest signal-change value is assigned at the temperature for the first signal-change value and two temperatures being apart from the temperature for the first signal-change value in the same interval are selected in both directions as the two reference temperatures.

27. The method according to claim 1, wherein the method further comprises calculating a real reaction Tm value of the duplex for each corresponding target nucleic acid sequence by using the signal values at three detection temperatures.

28. The method according to claim 1, wherein the two reference temperatures are selected such that a real reaction Tm value of the duplex for each corresponding target nucleic acid sequence is included between the two reference temperatures.

29. The method according to claim 1, wherein the signal-change value is obtained by a subtraction, a ratio or a change rate of the signal values.

30. The method according to claim 1, wherein the two reference detection temperatures for the plurality of target nucleic acid sequences are not overlapped with each other.

31. The method according to claim 1, wherein the two reference temperatures are selected by analyzing signal-change values for an identical target nucleic acid sequence in the single reaction vessel and different reaction vessels.

32. The method according to claim 1, wherein the signal-generating compositions comprise a composition which comprises a labeled oligonucleotide for generating a detectable signal by a cleavage reaction dependent on the presence of one of the plurality of target nucleic acid sequences, the labeled oligonucleotide is cleaved by a nuclease in the duplex reaction, and obtaining the signal values is performed at temperature at which all duplexes for the other target nucleic acid sequences of the plurality of target nucleic acid sequences are hybridized or dissociated to generate no signals; wherein the label in the labeled oligonucleotide for generating a detectable signal by a cleavage reaction has the same signal property to the labels in the duplexes.

33. The method according to claim 1, wherein the method further comprises restoring signal values from the data set of cycle/signal-change value for each corresponding target nucleic acid sequence to obtain a restored data set of cycle/signal value, and the determination of the presence or absence of the plurality of target nucleic acid sequences in the sample is performed by using the restored data set of cycle/signal value.

34. The method according to claim 33, wherein the restored signal values are signal values at temperature at which a duplex for each corresponding target nucleic acid sequence generates a highest signal value.

* * * * *